(12) United States Patent
Pfund

(10) Patent No.: US 6,362,403 B1
(45) Date of Patent: Mar. 26, 2002

(54) INBRED CORN PLANT FBLL

(75) Inventor: John H. Pfund, Sycamore, IL (US)

(73) Assignee: Dekalb Genetics Corporation, Dekalb, IL (US)

( * ) Notice: Subject to any disclaimer, the term of this patent is extended or adjusted under 35 U.S.C. 154(b) by 0 days.

(21) Appl. No.: 08/181,708

(22) Filed: Jan. 14, 1994

Related U.S. Application Data

(63) Continuation-in-part of application No. 08/164,621, filed on Dec. 7, 1993, now Pat. No. 5,436,389, which is a continuation of application No. 07/659,977, filed on Feb. 21, 1991, now abandoned.

(51) Int. Cl.$^7$ .............................. A01H 5/00; A01H 4/00; C12N 5/04
(52) U.S. Cl. ................... 800/320.1; 800/298; 800/275; 800/271; 800/268; 800/266; 435/412; 435/424; 435/430; 435/430.1
(58) Field of Search .............................. 800/200, 205, 800/250, DIG. 56, 320.1, 298, 275, 271, 268, 266, 301–303; 47/58.03, 58.05; 435/240.4, 240.45, 240.49, 412, 424, 430, 430.1

(56) References Cited

U.S. PATENT DOCUMENTS 5,276,263 A    1/1994  Foley ........................ 800/200

OTHER PUBLICATIONS

Smith et al. (1991) Crop Science vol. 31#4, pp 893–899.*
1988 Corn Seed Grower Contract (Foundation Contract).
1989 Seed Corn Grower Contract (Experimental Production Contract)
1991 Seed Showcase for DK570, p. 4.
1992 Seed Showcase for DK554, p. 3.
1992 Seed Showcase for DK522, p. 2.
1993 Seed Showcase for DK623, p. 3.
1993 Seed Showcase for DK591, p. 2.
1993 Seed Showcase for DK512, p. 2.
1994 Seed Showcase for Region A, for DK580.
Edallo et al., Chromosal Variation and Frequency Of Spontaneous Mutation Associated With In Vitro Culture and Plant Regeneration In Maize, *Maydica XXVI* (1981): 39–56.
R.L. Phillips et al., Cell/Tissue and In Vitro Manipulation, *Corn and Corn Improvement.* Sprague et al., eds. Ch. 5: 345–387.
R. Rieger et al., *Glossary of Genetics and Cytogenetics,* Springer–Verlag, pg. 116.
Wright, Commercial Hybrid Seed Production, *Hybridization of Crop Plants,* Fehr et al., eds. Ch. 8: 161–176, 1980.
Green et al., Plant Regeneration from Tissue Cultures of Maize, *Crop Science,* 15:417–421, 1975.
R. Wych, Production of Hybrid Seed Corn, *Corn and Corn Improvement,* Sprague et al., eds. Ch. 9: 565–607, 1988.
Hallauer, et al. Corn Breeding, *Corn and Corn Improvement* Sprague et al., eds. Ch. 8: 463–564, 1988.
Meghji, et al. Inbreeding Depression, Inbred and Hybrid Grain Yields, and Other Traits of Maize Genotypes Representing Three Eras, *Crop Science,* vol. 24: 545–549, 1984.
MBS, Inc. Genetics Handbook, 17th Ed. 1990.
Duvick, D., Genetic Contributions to Yield Gains of U.S. Hybrid Maize, 1930 to 1980, Genetic Contributions to Yield Gains of Five Major Crop Plants, *American Society of Agronomy, Inc. and Crop Science Society of America,* pgs. 15–48, 1984.
Gordon–Kamm, William J., et al., "Transformation of Maize Cells and Regeneration of Fertile Transgenic Plants," *The Plant Cell,* 2:603–618, 1990.
Rhodes, et al. "Genetically Transformed Maize Plants from Protoplasts," *Science* 240:204–207, 1988.
Green, et al. "Plant Regeneration in Tissue Cultures of Maize," *Maize for Biological Research,* Plant Molecular Biology Assoc. pp. 367–372, 1982.
Troyer, A.F. A Retrospective View of Corn Genetic Resources, *Journal of Heredity,* 81:17–24, 1990.
Armstrong et al. Establishment and Maintenance of Friable, Embryogenic Maize Callus and the Involvement of L–Proline, *Planta,* 164:207–214, (1985).
Poehlman, J.M. *Breeding Field Crops,* Third Edition, p. 469–481.
Sprague, G.F., *Corn and Corn Improvement,* Chapter 6—"Corn Breeding", p. 305–362 24. (1977).
PVPA Certificate No. 9100034 to FBLL, Sep. 30, 1991.

* cited by examiner

*Primary Examiner*—Gary Benzion
(74) *Attorney, Agent, or Firm*—Fulbright & Jaworski, LLP

(57) ABSTRACT

According to the invention, there is provided an inbred corn plant, designated FBLL. This invention thus relates to the plants and seeds of inbred corn plant FBLL and to methods for producing a corn plant produced by crossing the inbred plant FBLL with itself or with another corn plant. This invention further relates to hybrid corn seeds and plants produced by crossing the inbred plant FBLL with another corn plant and to crosses with related species. This invention further relates to the inbred and hybrid genetic complements of inbred corn plant FBLL, and also relates to the RFLP and genetic isozyme typing profiles of inbred corn, plant FBLL.

7 Claims, No Drawings

INBRED CORN PLANT FBLL

CROSS-REFERENCE TO RELATED APPLICATION

This application is a Continuation-In-Part of U.S. patent application Ser. No. 08/164,621 now U.S. Pat. No. 5,436,389, filed Dec. 7, 1993, which is a File-Wrapper-Continuation of U.S. patent application Ser. No. 07/659,977, filed Feb. 21, 1991, now abandoned, the disclosure of which are incorporated herein by reference.

TECHNICAL FIELD OF THE INVENTION

The present invention relates to the field of corn breeding. In particular, the present invention relates to an inbred corn plant designated FBLL and derivatives of that inbred plant.

BACKGROUND OF THE INVENTION

The goal of field crop breeding is to combine various desirable traits in a single variety/hybrid. Such desirable traits include greater yield, better stalks, better roots, resistance to insecticides, pests, and disease, tolerance to heat and drought, reduced time to crop maturity, better agronomic quality, and uniformity in germination times, stand establishment, growth rate, maturity, and fruit size.

Breeding techniques take advantage of a plant's method of pollination. There are two general methods of pollination: a plant self-pollinates if pollen from one flower is transferred to the same or another flower of the same plant. A plant cross-pollinates if pollen comes to it from a flower on a different plant.

Corn plants (*Zea mays* L.) can be bred by both self-pollination and cross-pollination. Both types of pollination involve the corn plant's flowers. Corn has separate male and female flowers on the same plant, located on the tassel and the ear, respectively. Natural pollination occurs in corn when wind blows pollen from the tassels to the silks that protrude from the tops of the ears.

Plants that have been self-pollinated and selected for type over many generations become homozygous at almost all gene loci and produce a uniform population of true breeding progeny, a homozygous plant. A cross between two such homozygous plants produce a uniform population of hybrid plants that are heterozygous for many gene loci. Conversely, a cross of two plants each heterozygous at a number of gene loci produces a population of hybrid plants that differ genetically and are not uniform.

The development of uniform corn plant hybrids requires the development of homozygous inbred plants, the crossing of these inbred plants, and the evaluation of the crosses. Pedigree breeding and recurrent selection breeding methods are used to develop inbred plants from breeding populations. Those breeding methods combine the genetic backgrounds from two or more inbred plants or various other broad-based sources into breeding pools from which new inbred plants are developed by selling and selection of desired phenotypes. The new inbreds are crossed with other inbred plants and the hybrids from these crosses are evaluated to determine which of those have commercial potential.

The pedigree breeding method for single-gene traits involves crossing two genotypes. Each genotype can have one or more desirable characteristics lacking in the other; or, each genotype can complement the other. If the two original parental genotypes do not provide all of the desired characteristics, other genotypes can be included in the breeding population. Superior plants that are the products of these crosses are selfed and selected in successive generations. Each succeeding generation becomes more homogeneous as a result of self-pollination and selection. Typically, this method of breeding involves five or more generations of selfing and selection: $S_1 \rightarrow S_2$; $S_2 \rightarrow S_3$; $S_3 \rightarrow S_4$; $S_4 \rightarrow S_5$, etc. After at least five generations, the inbred plant is considered genetically pure.

Backcrossing can also be used to improve an inbred plant. Backcrossing transfers a specific desirable trait from one inbred or source to an inbred that lacks that trait. This can be accomplished for example by first crossing a superior inbred (A) (recurrent parent) to a donor inbred (non-recurrent parent), which carries the appropriate gene(s) for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other genes. The last backcross generation would be selfed to give pure breeding progeny for the gene(s) being transferred.

A single cross hybrid corn variety is the cross of two inbred plants, each of which has a genotype which complements the genotype of the other. The hybrid progeny of the first generation is designated $F_1$. Preferred $F_1$ hybrids are more vigorous than their inbred parents. This hybrid vigor, or heterosis, is manifested in many polygenic traits, including markedly improved higher yields, better stalks, better roots, better uniformity and better insect and disease resistance. In the development of hybrids only the $F_1$ hybrid plants are sought. An $F_1$ single cross hybrid is produced when two inbred plants are crossed. A double cross hybrid is produced from four inbred plants crossed in pairs (A×B and C×D) and then the two $F_1$ hybrids are crossed again (A×B)×(C×D).

The development of a hybrid corn variety involves three steps: (1) the selection of plants from various germplasm pools; (2) the selfing of the selected plants for several generations to produce a series of inbred plants, which, although different from each other, each breed true and are highly uniform; and (3) crossing the selected inbred plants with unrelated inbred plants to produce the hybrid progeny ($F_1$). During the inbreeding process in corn, the vigor of the plants decreases. Vigor is restored when two unrelated inbred plants are crossed to produce the hybrid progeny ($F_1$). An important consequence of the homozygosity and homogeneity of the inbred plants is that the hybrid between any two inbreds is always the same. Once the inbreds that give a superior hybrid have been identified, hybrid seed can be reproduced indefinitely as long as the homogeneity of the inbred parents is maintained. Conversely, much of the hybrid vigor exhibited by $F_1$ hybrids is lost in the next generation ($F_2$). Consequently, seed from hybrid varieties is not used for planting stock. It is not generally beneficial for farmers to save seed of $F_1$ hybrids. Rather, farmers purchase $F_1$ hybrid seed for planting every year.

North American farmers plant over 70 million acres of corn at the present time and there are extensive national and international commercial corn breeding programs. A continuing goal of these corn breeding programs is to develop high-yielding corn hybrids that are based on stable inbred plants that maximize the amount of grain produced and minimize susceptibility to environmental stresses. To accomplish this goal, the corn breeder must select and develop superior inbred parental plants for producing hybrids.

BRIEF SUMMARY OF THE INVENTION

Ine one aspect, the present invention provides a corn plant designated FBLL. The present invention also provides seed of corn plant FBLL, which seed has ATCC Accession No. PTA-3713, and a corn plant having the functional and morphological characteristics of corn plant FBLL.

In another aspect, the present invention provides a tissue culture of corn plant FBLL. Preferably, a tissue culture comprises embryos, protoplast, meristematic cells or pollen. Still further, the present invention provides a corn plant regenerated from a tissue culture of this invention.

In yet another aspect, the present invention provides a process of preparing a corn plant comprising crossing a first parent corn plant with a second parent corn plant wherein at least one of the parent corn plants is inbred corn plant FBLL. In a preferred embodiment, crossing comprises planting in pollinating proximity seeds of the first and second parent corn plant; growing the seeds of said first and second parent corn plant into plants that bear flowers; emasculating the flowers of the first or second parent corn plant to produce an emasculated parent corn plant; allowing cross-pollination to occur between the first and second parent corn plant; and harvesting the seeds from the emasculated parent corn plant.

In one embodiment, the process comprises crossing a female corn plant with a male corn plant where either the female corn plant or the male corn plant is corn plant FBLL.

The present invention also contemplates a corn plant produced by a process comprising crossing a first parent corn plant with a second parent corn plant wherein at least one of the first and second parent corn plants is corn plant FBLL. In one embodiment, a corn plant produced by the process is an $F_1$ hybrid corn plant. In preferred embodiments, $F_1$ hybrid corn plants are hybrid corn plants DK512, DK522, DK554, DK570, DK591, or DK623. The present invention further contemplates seed of an $F_1$ hybrid corn plant.

In yet a further aspect, the invention provides an inbred genetic complement of corn plant FBLL. An inbred genetic complement is preferably contained in a seed, a corn plant, or a diploid plant cell. In a preferred embodiment, that inbred genetic complement comprises the RFLP genetic marker profile of Table 5, the genetic isozyme typing profile of Table 6, or both the RFLP genetic marker profile of Table 5 and the genetic isozyme typing profile of Table 6.

In another aspect, the present invention provides a hybrid genetic complement formed by the combination of a haploid genetic complement of corn plant FBLL with a haploid genetic complement of a second corn plant. In a preferred embodiment, the hybrid genetic complement is contained in a seed, corn plant, or diploid plant cell.

In another aspect, the present invention provides a corn plant regenerated from a tissue culture that comprises a hybrid genetic complement of this invention.

DETAILED DESCRIPTION OF THE INVENTION

I. DEFINITIONS

Barren Plants: Plants that are barren, i.e. lack an ear with grain, or have an ear with only a few scattered kernels.

Cg: *Colletotrichum graminicola* rating. Rating times 10 is approximately equal to percent total plant infection.

CLN: Corn lethal necrosis (combination of Maize Chlorotic Mottle Virus and Maize Dwarf Mosaic virus) rating: numerical ratings are based on a severity scale where 1=most resistant to 9=susceptible.

Cn: *Corynebacterium nebraskense* rating. Rating times 10 is approximately equal to percent total plant infection.

Cz: *Cercospora zeae-maydis* rating. Rating times 10 is approximately equal to percent total plant infection.

Dgg: *Diatraea grandiosella* girdling rating (values are percent plants girdled and stalk lodged).

Dropped Ears: Ears that have fallen from the plant to the ground.

Dsp: Disbrotica species root ratings (1=east affected to 9=severe pruning).

Ear-Attitude: The attitude or position of the ear at harvest scored as upright, horizontal, or pendant.

Ear-Cob Color: The color of the cob, scored as white, pink, red, or brown.

Ear-Cob Diameter: The average diameter of the cob measured at the midpoint.

Ear-Cob Strength: A measure of mechanical strength of the cobs to breakage, scored as strong or weak.

Ear-Diameter: The average diameter of the ear at its midpoint.

Ear-Dry Husk Color: The color of the husks at harvest scored as buff, red, or purple.

Ear-Fresh Husk Color: The color of the husks 1 to 2 weeks after pollination scored as green, red, or purple.

Ear-Husk Bract: The length of an average husk leaf scored as short, medium, or long.

Ear-Husk Cover: The average distance from the tip of the ear to the tip of the husks. Minimum value no less than zero.

Ear-Husk Opening: An evaluation of husk tightness at harvest scored as tight, intermediate, or open.

Ear-Length: The average length of the ear.

Ear-Number Per Stalk: The average number of ears per plant.

Ear-Shank Internodes: The average number of internodes on the ear shank.

Ear-Shank Length: The average length of the ear shank.

Ear-Shelling Percent: The average of the shelled grain weight divided by the sum of the shelled grain weight and cob weight for a single ear.

Ear-Silk Color: The color of the silk observed 2 to 3 days after silk emergence scored as green-yellow, yellow, pink, red, or purple.

Ear-Taper (Shape): The taper or shape of the ear scored as conical, semi-conical, or cylindrical.

Ear-Weight: The average weight of an ear.

Early Stand: The percent of plants that emerge from the ground as determined in the early spring.

ER: Ear rot rating (values approximate percent ear rotted).

Final Stand Count: The number of plants just prior to harvest.

GDUs to Shed: The number of growing degree units (GDUs) or heat units required for an inbred line or hybrid to have approximately 50 percent of the plants shedding pollen as measured from time of planting. Growing degree units are calculated by the Barger Method, where the heat units for a 24-hour period are calculated as GDUs=[Maximum daily temperature+Minimum daily temperature)/2]−50. The highest maximum daily temperature used is 86 degrees Fahrenheit and the lowest minimum temperature used is 50 degrees Fahrenheit. GDUs to shed is then determined by summing the individual daily values from planting date to the date of 50 percent pollen shed.

GDUs to Silk: The number of growing degree units for an inbred line or hybrid to have approximately 50 percent of the plants with silk emergence as measured from time of planting. Growing degree units are calculated by the same methodology as indicated in the GDUs to shed definition.

Hc2: *Helminthosporium carbonum* race 2 rating. Rating times 10 is approximately equal to percent total plant infection.

Hc3: *Helminthosporium carbonum* race 3 rating. Rating times 10 is approximately equal to percent total plant infection.

Hm: Helminthosporium Maydis race 0 rating. Rating times 10 is approximately equal to percent total plant infection.

Ht1: *Helminthosporium turcicum* race 1 rating. Rating times 10 is approximately equal to percent total plant infection.

Ht2: *Helminthosporium turcicum* race 2 rating. Rating times 10 is approximately equal to percent total plant infection.

HtG: +=Presence of *Ht* chlorotic-lesion type resistance. Rating times 10 is approximately equal to percent total plant infection.
−=Absence of a *Ht* chlorotic-lesion type resistance. Rating times 10 is approximately equal to percent total plant infection.
+/=Segregation of a *Ht* chlorotic-lesion type resistance. Rating times 10 is approximately equal to percent total plant infection.

Kernel-Aleurone Color: The color of the aleurone scored as white, pink, tan, brown, bronze, red, purple, pale purple, colorless, or variegated.

Kernel-Cap Color: The color of the kernel cap observed at dry stage, scored as white, lemon-yellow, yellow or orange.

Kernel-Endosperm Color: The color of the endosperm scored as white, pale yellow, or yellow.

Kernel-Endosperm Type: The type of endosperm scored as normal, waxy, or opaque.

Kernel-Grade: The percent of kernels that are classified as rounds.

Kernel-Length: The average distance from the cap of the kernel to the pedicel.

Kernel-Number Per Row: The average number of kernels in a single row.

Kernel-Pericarp Color: The color of the pericarp scored as colorless, red-white crown, tan, bronze, brown, light red, cherry red, or variegated.

Kernel-Row Direction: The direction of the kernel rows on the ear scored as straight, slightly curved, spiral, or indistinct (scattered).

Kernel-Row Number: The average number of rows of kernels on a single ear.

Kernel-Side Color: The color of the kernel side observed at the dry stage, scored as white, pale yellow, yellow, orange, red, or brown.

Kernel-Thickness: The distance across the narrow side of the kernel.

Kernel-Type: The type of kernel scored as dent, flint, or intermediate.

Kernel-Weight: The average weight of a predetermined number of kernels.

Kernel-Width: The distance across the flat side of the kernel.

Kz: *Kabatiella zeae* rating. Rating times 10 is approximately equal to percent total plant infection.

Leaf-Angle: Angle of the upper leaves to the stalk scored as upright (0 to 30 degrees), intermediate (30 to 60 degrees), or lax (60 to 90 degrees).

Leaf-Color: The color of the leaves 1 to 2 weeks after pollination scored as light green, medium green, dark green, or very dark green.

Leaf-Length: The average length of the primary ear leaf.

Leaf-Longitudinal Creases: A rating of the number of longitudinal creases on the leaf surface 1 to 2 weeks after pollination. Creases are scored as absent, few, or many.

Leaf-Marginal: Waves: A rating of the waviness of the leaf margin 1 to 2 weeks after pollination. Rated as none, few, or many.

Leaf-Number: The average number of leaves of a mature plant. Counting begins with the cotyledonary leaf and ends with the flag leaf.

Leaf-Sheath Anthocyanin: A rating of the level of anthocyanin in the leaf sheath 1 to 2 weeks after pollination, scored as absent, basal-weak, basal-strong, weak or strong.

Leaf-Sheath Pubescence: A rating of the pubescence of the leaf sheath. Ratings are taken 1 to 2 weeks after pollination and scored as light, medium, or heavy.

Leaf-Width: The average width of the primary ear leaf measured at its widest point.

LSS: Late season standability (values times 10 approximate percent plants lodged in disease evaluation plots).

Moisture: The moisture of the grain at harvest.

On1: Ostrinia Nubilalis 1st brood rating (1=resistant to 9=susceptible).

On2: Ostrinia Nubilalis 2nd brood rating (1=resistant to 9=susceptible).

Relative Maturity: A maturity rating based on regression analysis. The regression analysis is developed by utilizing check hybrids and their previously established day rating versus actual harvest moistures. Harvest moisture on the hybrid in question is determined and that moisture value is inserted into the regression equation to yield a relative maturity.

Root Lodging: Root lodging is the percentage of plants that root lodge. A plant is counted as root lodged if a portion of the plant leans from the vertical axis by approximately 30 degrees or more.

Seedling Color: Color of leaves at the 6 to 8 leaf stage.

Seedling Height: Plant height at the 6 to 8 leaf stage.

Seedling Vigor: A visual rating of the amount of vegetative growth on a 1 to 9 scale, where 9 equals best. The score is taken when the average entry in a trial is at the fifth leaf stage.

Selection Index: The selection index gives a single measure of hybrid's worth based on information from multiple traits. One of the traits that is almost always included is yield. Traits may be weighted according to the level of importance assigned to them.

Sr: *Sphacelotheca reiliana* rating is actual percent infection.

Stalk-Anthocyanin: A rating of the amount of anthocyanin pigmentation in the stalk. The stalk is rated 1 to 2 weeks after pollination as absent, basal-weak, basal-strong, weak, or strong.

Stalk-Brace Root Color: The color of the brace roots observed 1 to 2 weeks after pollination as green, red, or purple.

Stalk-Diameter: The average diameter of the lowest visible internode of the stalk.

Stalk-Ear Height: The average height of the ear measured from the ground to the point of attachment of the ear shank of the top developed ear to the stalk.

Stalk-Internode Direction: The direction of the stalk internode observed after pollination as straight or zigzag.

Stalk-Internode Length: The average length of the internode above the primary ear.

Stalk Lodging: The percentage of plants that did stalk lodge. Plants are counted as stalk lodged if the plant is broken over or off below the ear.

Stalk-Nodes With Brace Roots: The average number of nodes having brace roots per plant.

Stalk-Plant Height: The average height of the plant as measured from the soil to the tip of the tassel.

Stalk-Tillers: The percent of plants that have tillers. A tiller is defined as a secondary shoot that has developed as a tassel capable of shedding pollen.

Staygreen: Staygreen is a measure of general plant health near the time of black layer formation (physiological maturity). It is usually recorded at the time the ear husks of most entries within a trial have turned a mature color. Scoring is on a 1 to 9 basis where 9 equals best.

STR: Stalk rot rating (values represent severity rating of 1=25 percent of inoculated internode rotted to 9=entire stalk rotted and collapsed).

SVC: Southeastern Virus Complex combination of Maize Chlorotic Dwarf Virus and Maize Dwarf Mosaic Virus) rating; numerical ratings are based on a severity scale where 1=most resistant to 9=susceptible (1988 reactions are largely Maize Dwarf Mosaic Virus reactions).

Tassel-Anther Color: The color of the anthers at 50 percent pollen shed scored as green-yellow, yellow, pink, red, or purple.

Tassel-Attitude: The attitude of the tassel after pollination scored as open or compact.

Tassel-Branch Angle: The angle of an average tassel branch to the main stem of the tassel scored as upright (less than 30 degrees), intermediate (30 to 45 degrees), or lax (greater than 45 degrees).

Tassel-Branch Number: The average number of primary tassel branches.

Tassel-Glume Band: The closed anthocyanin band at the base of the glume scored as present or absent.

Tassel-Glume Color: The color of the glumes at 50 percent shed scored as green, red, or purple.

Tassel-Length: The length of the tassel measured from the base of the bottom tassel branch to the tassel tip.

Tassel-Peduncle Length: The average length of the tassel peduncle, measured from the base of the flag leaf to the base of the bottom tassel branch.

Tassel-Pollen Shed: A visual rating of pollen shed determined by tapping the tassel and observing the pollen flow of approximately five plants per entry. Rated on a 1 to 9 scale where 9=sterile, 1=most pollen.

Tassel-Spike Length: The length of the spike measured from the base of the top tassel branch to the tassel tip.

Test Weight: The measure of the weight of the grain in pounds for a given volume (bushel) adjusted to 15.5 percent moisture.

Yield: Yield of grain at harvest adjusted to 15.5 percent moisture.

II. OTHER DEFINITIONS

Allele is any of one or more alternative forms of a gene, all of which alleles relate to one trait or characteristic. In a diploid cell or organism, the two alleles of a given gene occupy corresponding loci on a pair of homologous chromosomes.

Backcrossing is a process in which a breeder crosses a first generation hybrid ($F_1$) with one of the parental genotypes.

Chromatography is a technique wherein a mixture of dissolved substances are bound to a solid support followed by passing a column of fluid across the solid support and varying the composition of the fluid. The components of the mixture are separated by selective elution.

Crossing refers to the mating of two parent plants.

Cross-pollination refers to fertilization by the union of two gametes from different plants.

Diploid refers to a cell or organism having two sets of chromosomes.

Electrophoresis is a process by which particles suspended in a fluid are moved under the action of an electrical field, and thereby separated according to their charge and molecular weight. This method of separation is well known to those skilled in the art and is typically applied to separating various forms of enzymes and of DNA fragments produced by restriction endonucleases.

Emasculate refers to the removal of plant male sex organs.

Enzymes are organic catalysts that can exist in various forms called isozymes.

$F_1$ refers to the first generation progeny of the cross of two plants.

Genetic Complement refers to an aggregate of nucleotide sequences, the expression of which sequences defines the phenotype in corn plants, or components of plants including cells or tissue.

Genotype refers to the genetic constitution of a cell or organism.

Haploid refers to a cell or organism having one set of the two sets of chromosomes in a diploid.

Isozymes are one of a number of enzymes which catalyze the same reaction(s) but differ from each other, e.g. in primary structure and/or electrophoretic mobility. The differences between isozymes are under single gene, codominant control. Consequently, electrophoretic separation to produce band patterns can be equated to different alleles at the DNA level. Structural differences that do not alter charge cannot be detected by this method.

Isozyme typing profile refers to a profile of band patterns of isozymes separated by electrophoresis that can be equated to different alleles at the DNA level.

Linkage refers to a phenomenon wherein alleles on the same chromosome tend to segregate together more often than expected by chance if their transmission was independent.

Marker is a readily detectable phenotype, preferably inherited in codominant fashion (both alleles at a locus in a diploid heterozygote are readily detectable), with no environmental variance component, i.e., heritability of 1.

FBLL refers to the corn plant from which seeds having ATCC accession No. PTA-3713 were obtained as well as a plant grown from those seeds.

Phenotype refers to the detectable characteristics of a cell or organism, which characteristics are the manifestation of gene expression.

Quantitative Trait Loci (QTL) refer to genetic loci that control to some degree numerically representable traits that are usually continuously distributed.

Regeneration refers to the development of a plant from tissue culture.

RFLP genetic marker profile refers to a profile of band patterns of DNA fragment lengths typically separated by agarose gel electrophoresis, after restriction endonuclease digestion of DNA.

Self-pollination refers to the transfer of pollen from the anther to the stigma of the same plant.

Tissue Culture refers to a composition comprising isolated cells of the same or a different type or a collection of such cells organized into parts of a plant.

III. INBRED CORN PLANT FBLL

In accordance with one aspect of the present invention, there is provided a novel inbred corn plant, designated FBLL. Inbred corn plant FBLL is a yellow, dent corn inbred that resembles inbred corn plant B73HT. Inbred FBLL has, as one of its parents, PB80, a proprietary inbred of DEKALB Plant Genetics. FBLL differs significantly (at the 5 percent level) from B73HT and PB80 in several aspects (See Table 1).

tained separately. In the summer of 1984, the thirty (30) $S_2$ ears were grown ear-to-row. A total of thirty-five (35) self-pollinated $S_3$ ears were selected from the thirty (30) rows and each of the thirty-five (35) ears were shelled separately. In the summer of 1985, the thirty-five (35) $S_3$ ears were grown on an ear-to-row basis. Twenty-four (24) self-pollinated $S_4$ ears were selected, harvested, and shelled individually. In the winter of 1986, four (4) of the twenty-four (24) $S_4$'s were grown ear-to-row. Ears from two (2) self-pollinated plants were selected. These ears were given the designation FBLL.

FBLL shows uniformity and stability within the limits of environmental influence for the traits described hereinafter in Table 2. FBLL has been self-pollinated and ear-rowed a sufficient number of generations with careful attention paid to uniformity of plant type to ensure homozygosity and phenotypic stability. No variant traits have been observed or are expected in FBLL.

A deposit of 2500 seeds of plant designated FBLL has been made with the American Type Culture Collection, Rockville Pike, Bethesda, Md. on Sep. 20, 2001. Those deposited seeds have been assigned Accession No. PTA-3713. The deposit was made in accordance with the terms and provisions of the Budapest Treaty relating to deposit of microorganisms and is made for a term of at least thirty (30) years and at least five (05) years after the most recent request

TABLE 1

COMPARISON OF FBLL WITH B73HT AND PB80

| INBRED | BARREN % | DROP % | EHT INCH | FINAL | MST % | PHT INCH | RTL % | SHED GDU | SILK GDU | STL % | YLD BU/A |
|---|---|---|---|---|---|---|---|---|---|---|---|
| FBLL | 3.1 | 0.1 | 27.9 | 58.3 | 19.5 | 70.5 | 0.0 | 1459.1 | 1483.7 | 1.8 | 84.5 |
| B73HT | 3.2 | 0.3 | 34.6 | 59.0 | 20.9 | 79.4 | 0.1 | 1558.3 | 1570.7 | 1.9 | 82.2 |
| DIFF | 0.1 | −0.2 | −6.7 | −0.8 | −1.4 | −8.8 | −0.1 | −99.2 | −87.0 | 0.2 | 2.4 |
| # LOC/TESTS | 11 | 26 | 26 | 26 | 26 | 26 | 26 | 26 | 26 | 26 | 26 |
| P VALUE | 0.88 | 0.36 | 0.00** | 0.26 | 0.09+ | 0.00** | 0.94 | 0.00** | 0.00** | 0.69 | 0.42 |
| FBLL | 2.0 | 0.2 | 30.9 | 54.6 | 19.8 | 70.6 | 0.4 | 1491.0 | 1526.0 | 2.6 | 73.2 |
| PB80 | 1.7 | 0.5 | 35.8 | 56.7 | 19.3 | 76.1 | 1.0 | 1495.1 | 1516.2 | 3.1 | 88.0 |
| DIFF | 0.3 | −0.3 | −4.9 | −2.1 | 0.4 | −5.5 | −0.7 | −4.1 | 9.8 | −0.5 | −14.8 |
| # LOC/TESTS | 26 | 50 | 49 | 50 | 50 | 49 | 50 | 50 | 50 | 50 | 50 |
| P VALUE | 0.34 | 0.22 | 0.00** | 0.00** | 0.21 | 0.00** | 0.46 | 0.23 | 0.11 | 0.31 | 0.00** |

Legend Abbreviations
BARREN % = Barren Plants (Percent)
DROP % = Dropped Ears (Percent)
EHT INCH = Ear Height (Inches)
FINAL = Final Stand
MST % = Moisture (Percent)
PHT INCH = Plant Height (Inches)
RTL % = Root Lodging (Percent)
SHED GDU = GDUs to Shed
SILK GDU = GDUs to Silk
STL % = Stalk Lodging (Percent)
YLD BU/A = Yield (Bushels/Acre)
Significance levels are indicated as:
+ = 10 percent
* = 5 percent
** = 1 percent

A. Origin and Breeding History

Inbred plant FBLL was derived from a cross made in the summer of 1982 between 5B2C-A and PB80. Both 5B2C-A and PB80 are proprietary inbred lines of DEKALB Plant Genetics. In the winter of 1982, $S_0$ seed was grown and individual plants were self-pollinated. The resulting $S_1$ seed was harvested, bulked, and planted in the summer of 1983. The ears from thirty (30) individual self-pollinated plants were selected at harvest and ears were shelled and mainfor the furnishing of a sample of the deposit was received by the depository. most recent request for the furnishing of a sample of the deposit was received by the depository, or for the effective term of the patent, whichever is longer, and will be replaced if it becomes non-viable during that period.

Inbred corn plants can be reproduced by planting such inbred seeds, growing the resulting corn plants under self-pollinating or sib-pollinating conditions with adequate isolation using standard techniques well known to an artisan skilled in the agricultural arts. Seeds can be harvested from such a plant using standard, well known procedures.

B. Phenotypic Description

In accordance with another aspect of the present invention, there is provided a corn plant having the functional and morphological characteristics of corn plant FBLL. A description of the functional and morphological characteristics of corn plant FBLL is presented below in Table 2.

TABLE 2

MORPHOLOGICAL TRAITS FOR THE FBLL PHENOTYPE

| CHARACTERISTIC | VALUE |
| --- | --- |
| 1. Stalk | |
| Diameter (Width) cm. | 2.2 |
| Anthocyanin | ABSENT |
| Nodes With Brace Roots | 2.3 |
| Internode Direction | STRAIGHT |
| Internode Length cm. | 14.6 |
| 2. Leaf | |
| Angle | UPRIGHT |
| Number | 18.9 |
| Color | MEDIUM GREEN |
| Length cm. | 72.2 |
| Width cm. | 8.8 |
| Marginal Waves | FEW |
| Longitudinal Creases | FEW |
| 3. Tassel | |
| Length cm. | 26.7 |
| Spike Length cm. | 17.9 |
| Peduncle Length cm. | 9.5 |
| Attitude | COMPACT |
| Branch Angle | UPRIGHT |
| Branch Number | 5.9 |
| Glume Color | GREEN |
| Glume Band | ABSENT |
| 4. Ear | |
| Silk Color | GREEN-YELLOW |
| Number Per Stalk | 1.1 |
| Position (Attitude) | UPRIGHT |
| Length cm. | 14.4 |
| Shape | SEMI-CONICAL |
| Diameter cm. | 4.1 |
| Weight gm. | 122.4 |
| Shank Length cm. | 9.0 |
| Shank Internode Number | 7.1 |
| Husk Bract | SHORT |
| Husk Cover cm. | 5.1 |
| Husk Color Fresh | GREEN |
| Husk Color Dry | BUFF |
| Cob Diameter cm. | 2.4 |
| Cob Color | RED |
| Cob Strength | STRONG |
| Shelling Percent | 83.5 |
| 5. Kernel | |
| Row Number | 17.3 |
| Number Per Row | 28.9 |
| Row Direction | CURVED |
| Type | DENT |
| Length (Depth) mm. | 11.4 |
| Width mm. | 6.9 |
| Thickness | 4.2 |
| Weight of 1000K gm. | 233.6 |
| Endosperm Type | NORMAL |
| Endosperm Color | YELLOW |

\* These are typical values. Values may vary due to environment. Other values that are substantially equivalent are also within the scope of the invention. Substantially equivalent refers to quantitative traits that when compared do not show statistical differences of their means.

IV. TISSUE CULTURE AND IN VITRO REGENERATION OF A CORN PLANT

A further aspect of the invention relates to tissue culture of corn plant FBLL. As used herein, the term "tissue culture" indicates a composition comprising isolated cells of the same or a different type or a collection of such cells organized into parts of a plant. Exemplary types of tissue cultures are plant protoplast, plant calli, plant clumps, and plant cells that are intact in plants or parts of plants, such as embryos, pollen, flowers, kernels, ears, cobs, leaves, husks, stalks, roots, root tips, anthers, and silk and the like. In a preferred embodiment, tissue culture is embryos, protoplast, meristematic cells, pollen, leaves or anthers. Means for preparing and maintaining plant tissue culture are well known in the art. By way of example, a tissue culture comprising organs such as tassels or anthers, has been used to produce regenerated plants. (See, U.S. patent application Ser. Nos. 07/992,637, filed Dec. 18, 1992 and 07/995,938, filed Dec. 21, 1992, now issued as U.S. Pat. No. 5,322,798 on Jun. 21, 1994 the disclosures of which are incorporated herein by reference).

A. Tassel/Anther Culture

Tassels contain anthers which in turn enclose microspores. Microspores develop into pollen. For anther/microspore culture, if tassels are the plant composition, they are preferably selected at a stage when the microspores are uninucleate, that is, include only one, rather than 2 or 3 nucléi. Methods to determine the correct stage are well known to those skilled in the art and include mitramycin fluorescent staining (Pace et al., 1987), trypan blue (preferred) and acetocarmine squashing. The mid-uninucleate microspore stage has been found to be the developmental stage most responsive to the subsequent methods disclosed to ultimately produce plants.

Although microspore-containing plant organs such as tassels can generally be pretreated at any cold temperature below about 25° C., a range of 4 to 25° C. is preferred, and a range of 8 to 14° C. is particularly preferred. Although other temperatures yield embryoids and regenerated plants, cold temperatures produce optimum response rates compared to pretreatment at temperatures outside the preferred range. Response rate is measured as either the number of embryoids or the number of regenerated plants per number of microspores initiated in culture.

Although not required, when tassels are employed as the plant organ, it is generally preferred to sterilize their surface. Following surface sterilization of the tassels, for example, with a solution of calcium hypochloride, the anthers are removed from about 70 to 150 spikelets (small portions of the tassels) and placed in a preculture or pretreatment medium. Larger or smaller amounts can be used depending on the number of anthers.

When one elects to employ tassels directly, tassels are preferably pretreated at a cold temperature for a predefined time, preferably at 10° C. for about 4 days. After pretreatment of a whole tassel at a cold temperature, dissected anthers are further pretreated in an environment that diverts microspores from their developmental pathway. The function of the preculture medium is to switch the developmental program from one of pollen development to that of embryoid/callus development. An embodiment of such an environment in the form of a preculture medium includes a sugar alcohol, for example mannitol or sorbitol, inositol or the like. An exemplary synergistic combination is the use of mannitol at a temperature of about 10° C. for a period ranging from about 10 to 14 days. In a preferred embodiment, 3 ml of 0.3 M mannitol combined with 50 mg/l of ascorbic acid, silver nitrate and colchicine is used for incubation of anthers at 10° C. for between 10 and 14 days. Another embodiment is to substitute sorbitol for mannitol. The colchicine produces chromosome doubling at this early stage. The chromosome doubling agent is preferably only present at the preculture stage.

It is believed that the mannitol or other similar carbon structure or environmental stress induces starvation and functions to force microspores to focus their energies on entering developmental stages. The cells are unable to use, for example, mannitol as a carbon source at this stage. It is believed that these treatments confuse the cells causing them to develop as embryoids and plants from microspores. Dramatic increases in development from these haploid cells, as high as 25 embryoids in $10_4$ microspores, have resulted from using these methods.

In embodiments where microspores are obtained from anthers, microspores can be released from the anthers into an isolation medium following the mannitol preculture step. One method of release is by disruption of the anthers, for example, by chopping the anthers into pieces with a sharp instrument, such as a razor blade, scalpel or Waring blender. The resulting mixture of released microspores, anther fragments and isolation medium are then passed through a filter to separate microspores from anther wall fragments. An embodiment of a filter is a mesh, more specifically, a nylon mesh of about 112 $\mu$m pore size. The filtrate which results from filtering the microspore-containing solution is preferably relatively free of anther fragments, cell walls and other debris.

In a preferred embodiment, isolation of microspores is accomplished at a temperature below about 25° C. and, preferably at a temperature of less than about 15° C. Preferably, the isolation media, dispersing tool (e.g., razor blade) funnels, centrifuge tubes and dispersing container (e.g., petri dish) are all maintained at the reduced temperature during isolation. The use of a precooled dispersing tool to isolate maize microspores has been reported (Gaillard, et al., 1991).

Where appropriate and desired, the anther filtrate is then washed several times in isolation medium. The purpose of the washing and centrifugation is to eliminate any toxic compounds which are contained in the non-microspore part of the filtrate and are created by the chopping process. The centrifugation is usually done at decreasing spin speeds, for example, 1000, 750, and finally 500 rpms.

The result of the foregoing steps is the preparation of a relatively pure tissue culture suspension of microspores that are relatively free of debris and anther remnants.

To isolate microspores, an isolation media is preferred. An isolation media is used to separate microspores from the anther walls while maintaining their viability and embryogenic potential. An illustrative embodiment of an isolation media includes a 6 percent sucrose or maltose solution combined with an antioxidant such as 50 mg/l of ascorbic acid, 0.1 mg/l biotin and 400 mg/l of proline, combined with 10 mg/l of nicotinic acid and 0.5 mg/l $AgNO_3$. In another embodiment, the biotin and proline are omitted.

An isolation media preferably has a higher antioxidant level where used to isolate microspores from a donor plant (a plant from which a plant composition containing a microspore is obtained) that is field grown in contrast to greenhouse grown. A preferred level of ascorbic acid in an isolation medium is from about 50 mg/l to about 125 mg/l and, more preferably from about 50 mg/l to about 100 mg/l.

One can find particular benefit in employing a support for the microspores during culturing and subculturing. Any support that maintains the cells near the surface can be used. The microspore suspension is layered onto a support, for example by pipetting. There are several types of supports which are suitable and are within the scope of the invention. An illustrative embodiment of a solid support is a TRANSWELL® culture dish. Another embodiment of a solid support for development of the microspores is a bilayer plate wherein liquid media is on top of a solid base. Other embodiments include a mesh or a millipore filter. Preferably, a solid support is a nylon mesh in the shape of a raft. A raft is defined as an approximately circular support material which is capable of floating slightly above the bottom of a tissue culture vessel, for example, a petri dish, of about a 60 or 100 mm size, although any other laboratory tissue culture vessel will suffice. In an illustrative embodiment, a raft is about 55 mm in diameter.

Culturing isolated microspores on a solid support, for example, on a 10 $\mu$m pore nylon raft floating on 2.2 ml of medium in a 60 mm petri dish, prevents microspores from sinking into the liquid medium and thus avoiding low oxygen tension. These types of cell supports enable the serial transfer of the nylon raft with its associated microspore-embryoids ultimately to full strength medium containing activated charcoal and solidified with, for example, GELRITE™ (solidifying agent). The charcoal is believed to absorb toxic wastes and intermediaries. The solid medium allows embryoids to mature.

The liquid medium passes through the mesh while the microspores are retained and supported at the medium-air interface. The surface tension of the liquid medium in the petri dish causes the raft to float. The liquid is able to pass through the mesh: consequently, the microspores stay on top. The mesh remains on top of the total volume of liquid medium. An advantage of the raft is to permit diffusion of nutrients to the microspores. Use of a raft also permits transfer of the microspores from dish to dish during subsequent subculture with minimal loss, disruption or disturbance of the induced embryoids that are developing. The rafts represent an advantage over the multi-welled TRANSWELL® plates, which are commercially available from COSTAR, in that the commercial plates are expensive. Another disadvantage of these plates is that to achieve the serial transfer of microspores to subsequent media, the membrane support with cells must be peeled off the insert in the wells. This procedure does not produce as good a yield nor as efficient transfers, as when a mesh is used as a vehicle for cell transfer.

The culture vessels can be further defined as either (1) a bilayer 60 mm petri plate wherein the bottom 2 ml of medium are solidified with 0.7 percent agarose overlayed with 1 mm of liquid containing the microspores; (2) a nylon mesh raft wherein a wafer of nylon is floated on 1.2 ml of medium and 1 ml of isolated microspores is pipetted on top; or (3) TRANSWELL® plates wherein isolated microspores are pipetted onto membrane inserts which support the microspores at the surface of 2 ml of medium.

After the microspores have been isolated, they are cultured in a low strength anther culture medium until about the 50 cell stage when they are subcultured onto an embryoid/callus maturation medium. Medium is defined at this stage as any combination of nutrients that permit the microspores to develop into embryoids or callus. Many examples of suitable embryoid/callus promoting media are well known to those skilled in the art. These media will typically comprise mineral salts, a carbon source, vitamins, growth regulations. A solidifying agent is optional. A preferred embodiment of such a media is referred to by the inventor as the "D medium" which typically includes 6N1 salts, $AgNO_3$ and sucrose or maltose.

In an illustrative embodiment, 1 ml of isolated microspores are pipetted onto a 10 $\mu$m nylon raft and the raft is floated on 1.2 ml of medium "D", containing sucrose or, preferably maltose. Both calli and embryoids can develop. Calli are undifferentiated aggregates of cells. Type I is a relatively compact, organized and slow growing callus. Type II is a soft, friable and fast-growing one. Embryoids are aggregates exhibiting some embryo-like structures. The embryoids are preferred for subsequent steps to regenerating plants. Culture medium "D" is an embodiment of medium that follows the isolation medium and replaces it. Medium "D" promotes growth to an embryoid/callus. This medium comprises 6N1 salts at ⅛ the strength of a basic stock solution, (major components) and minor components, plus 12 percent sucrose or, preferably 12 percent maltose, 0.1 mg/l B1, 0.5 mg/l nicotinic acid, 400 mg/l proline and 0.5 mg/l silver nitrate. Silver nitrate is believed to act as an inhibitor to the action of ethylene. Multi-cellular structures of approximately 50 cells each generally arise during a period of 12 days to 3 weeks. Serial transfer after a two week incubation period is preferred.

After the petri dish has been incubated for an appropriate period of time, preferably two weeks, in the dark at a predefined temperature, a raft bearing the dividing microspores is transferred serially to solid based media which promotes embryo maturation. In an illustrative embodiment, the incubation temperature is 30° C. and the mesh raft supporting the embryoids is transferred to a 100 mm petri dish containing the 6N1-TGR-4P medium, an "anther culture medium." This medium contains 6N1 salts, supplemented with 0.1 mg/l TIBA, 12 percent sugar (sucrose, maltose or a combination thereof), 0.5 percent activated charcoal, 400 mg/l proline, 0.5 mg/l B, 0.5 mg/l nicotinic acid, and 0.2 percent GELRITE™ (solidifying agent) and is capable of promoting the maturation of the embryoids. Higher quality embryoids, that is, embryoids which exhibit more organized development, such as better shoot meristem formation without precocious germination were typically obtained with the transfer to full strength medium compared to those resulting from continuous culture using only, for example, the isolated microspore culture (IMC) Medium "D." The maturation process permits the pollen embryoids to develop further in route toward the eventual regeneration of plants. Serial transfer occurs to full strength solidified 6N1 medium using either the nylon raft, the TRANSWELL™ membrane or bilayer plates, each one requiring the movement of developing embryoids to permit further development into physiologically more mature structures.

In an especially preferred embodiment, microspores are isolated in an isolation media comprising about 6 percent maltose, cultured for about two weeks in an embryoid/calli induction medium comprising about 12 percent maltose and then transferred to a solid medium comprising about 12 percent sucrose.

At the point of transfer of the raft after about two weeks incubation, embryoids exist on a nylon support. The purpose of transferring the raft with the embryoids to a solidified medium after the incubation is to facilitate embryo maturation. Mature embryoids at this point are selected by visual inspection indicated by zygotic embryo-like dimensions and structures and are transferred to the shoot initiation medium. It is preferred that shoots develop before roots, or that shoots and roots develop concurrently. If roots develop before shoots, plant regeneration can be impaired. To produce solidified media, the bottom of a petri dish of approximately 100 mm is covered with about 30 ml of 0.2 percent GELRITE™ (solidifying agent) solidified medium. A sequence of regeneration media are used for whole plant formation from the embryoids.

During the regeneration process, individual embryoids are induced to form plantlets. The number of different media in the sequence can vary depending on the specific protocol used. Finally, a rooting medium is used as a prelude to transplanting to soil. When plantlets reach a height of about 5 cm, they are then transferred to pots for further growth into flowering plants in a greenhouse by methods well known to those skilled in the art.

Plants have been produced from isolated microspore cultures by methods disclosed herein, including self-pollinated plants. The rate of embryoid induction was much higher with the synergistic preculture treatment consisting of a combination of stress factors, including a carbon source which can be capable of inducing starvation, a cold temperature and colchicine, than has previously been reported. An illustrative embodiment of the synergistic combination of treatments leading to the dramatically improved response rate compared to prior methods, is a temperature of about 10° C., mannitol as a carbon source, and 0.05 percent colchicine.

The inclusion of ascorbic acid, an anti-oxidant, in the isolation medium is preferred for maintaining good microspore viability. However, there seems to be no advantage to including mineral salts in the isolation medium. The osmotic potential of the isolation medium was maintained optimumly with about 6 percent sucrose, although a range of 2 percent to 12 percent is within the scope of this invention.

In an embodiment of the embryoid/callus organizing media, mineral salts concentration in IMC Culture Media "D" is (⅛×), the concentration which is used also in anther culture medium. The 6N1 salts major components have been modified to remove ammonium nitrogen. Osmotic potential in the culture medium is maintained with about 12 percent sucrose and about 400 mg/l proline. Silver nitrate (0.5 mg/l) was included in the medium to modify ethylene activity. The preculture media is further characterized by having a pH of about 5.7 to 6.0. Silver nitrate and vitamins do not appear to be crucial to this medium but do improve the efficiency of the response.

Whole anther cultures can also be used in the production of monocotyledonous plants from a plant culture system. There are some basic similarities of anther culture methods and microspore culture methods with regard to the media used. A difference from isolated microspore cultures is that undisrupted anthers are cultured, so that a support, e.g. a nylon mesh support, is not needed. The first step in developing the anther cultures is to incubate tassels at a cold temperature. A cold temperature is defined as less than about 25° C. More specifically, the incubation of the tassels is preferably performed at about 10° C. A range of 8 to 14° C. is also within the scope of the invention. The anthers are then dissected from the tassels, preferably after surface sterilization using forceps, and placed on solidified medium. An example of such a medium is designated by the inventors as 6N1-TGR-P4.

The anthers are then treated with environmental conditions that are combinations of stresses that are capable of diverting microspores from gametogenesis to embryogenesis. It is believed that the stress effect of sugar alcohols in the preculture medium, for example, mannitol, is produced by inducing starvation at the predefined temperature. In one embodiment, the incubation pretreatment is for about 14 days at 10° C. It was found that treating the anthers in addition with a carbon structure, an illustrative embodiment being a sugar alcohol, preferably, mannitol, produces dramatically higher anther culture response rates as measured by the number of eventually regenerated plants, than by treatment with either cold treatment or mannitol alone. These results are particularly surprising in light of teachings that cold is better than mannitol for these purposes, and that warmer temperatures interact with mannitol better.

To incubate the anthers, they are floated on a preculture medium which diverts the microspores from gametogenesis, preferably on a mannitol carbon structure, more specifically, 0.3 M of mannitol plus 50 mg/l of ascorbic acid. 3 ml is about the total amount in a dish, for example, a tissue culture dish, more specifically, a 60 mm petri dish. Anthers are isolated from about 120 spikelets for one dish yields about 360 anthers.

Chromosome doubling agents can be used in the preculture media for anther cultures. Several techniques for doubling chromosome number (Jensen 1974; Wan, et al. 1989) have been described. Colchicine is one of the doubling agents. However, developmental abnormalities arising from in vitro cloning are further enhanced by colchicine treatments, and previous reports indicated that colchicine is toxic to microspores. The addition of colchicine in increasing concentrations during mannitol pretreatment prior to anther culture and microspore culture has achieved improved percentages.

An illustrative embodiment of the combination of a chromosome doubling agent and preculture medium is one which contains colchicine. In a specific embodiment, the colchicine level is preferably about 0.05 percent. The anthers remain in the mannitol preculture medium with the additives for about 10 days at 10° C. Anthers are then placed on maturation media, for example, that designated 6N1-TGR-P4, for 3 to 6 weeks to induce embryoids. If the plants are to be regenerated from the embryoids, shoot regeneration medium is employed, as in the isolated microspore procedure described in the previous sections. Other regeneration media can be used sequentially to complete regeneration of whole plants.

The anthers are then exposed to embryoid/callus promoting medium, for example, that designated 6N1-TGR-P4 to obtain callus or embryoids. The embryoids are recognized by identification visually of embryonic-like structures. At this stage, the embryoids are transferred serially to a series of regeneration media. In an illustrative embodiment, the shoot initiation medium comprises BAP (6-benzyl-aminopurine) and NAA (naphthalene acetic acid). Regeneration protocols for isolated microspore cultures and anther cultures are similar.

B. Other Cultures and Regeneration

The present invention contemplates a corn plant regenerated from a tissue culture of an inbred (e.g. FBLL), or hybrid plant (DK512, DK522, DK554, DK570, DK591, or DK623) of the present invention. As is well known in the art, tissue culture of corn can be used for the in vitro regeneration of a corn plant. By way of example, a process of tissue culturing and regeneration of corn is described in European Patent Application, publication 160,390, the disclosure of which is incorporated by reference. Corn tissue culture procedures are also described in Green and Rhodes, "Plant Regeneration in Tissue Culture of Maize," *Maize for Biological Research* (Plant Molecular Biology Association, Charlottesville, Va. 1982, at 367–372, U.S. Pat. No. 5,134,074, and Duncan et al. "The Production of Callus Capable of Plant Regeneration from Immature Embryos of Numerous Zea Mays Genotypes," *Planta* 165:322–332 (1985). The study by Duncan indicates that 97 percent of cultured plants produced calli capable of regenerating plants. Subsequent studies have shown that both inbreds and hybrids produced 91 percent regenerable calli that produced plants.

Other studies indicate that non-traditional tissues are capable of producing somatic embryogenesis and plant regeneration. See, e.g. "Plant Regeneration from Maize Callus Cultures," *Plant Cell Reports*, 7:262–265 (1988), K. V. Rao et. al., "Somatic Embryogenesis in Glume Callus Cultures," Maize Genetics Cooperation Newsletter, Vol. 60 (1986), and Conger, B. V., et al., "Somatic Embryogenesis from Cultured Leaf Segments of Zea Mays," Plant Cell Reports 6:345–347 (1987), the disclosures of which are incorporated herein by reference.

Briefly, by way of example, to regenerate a plant of this invention, cells are selected following growth in culture. Where employed, cultured cells are preferably grown either on solid supports or in the form of liquid suspensions as set forth above. In either instance, nutrients are provided to the cells in the form of media, and environmental conditions are controlled. There are many types of tissue culture media comprising amino acids, salts, sugars, hormones and vitamins. Most of the media employed to regenerate inbred and hybrid plants have some similar components, the media differ in the composition and proportions of their ingredients depending on the particular application envisioned. For example, various cell types usually grow in more than one type of media, but exhibit different growth rates and different morphologies, depending on the growth media. In some media, cells survive but do not divide. Various types of media suitable for culture of plant cells have been previously described and discussed above.

An exemplary embodiment for culturing recipient corn cells in suspension cultures includes using embryogenic cells in Type II (Armstrong and Green, 1985; Gordon-Kamm et al., 1990) callus, selecting for small (10 to 30 $\mu$) isodiametric, cytoplasmically dense cells, growing the cells in suspension cultures with hormone containing media, subculturing into a progression of media to facilitate development of shoots and roots, and finally, hardening the plant and readying it metabolically for growth in soil.

Meristematic cells (i.e., plant cells capable of continual cell division and characterized by an undifferentiated cytological appearance, normally found at growing points or tissues in plants such as root tips, stem apices, lateral buds, etc.) can be cultured.

Embryogenic calli are produced (Gordon-Kamm, et al., 1990). Specifically, plants from hybrids produced from crossing an inbred of the present invention with another inbred are grown to flowering in a greenhouse. Explants from at least one of the following $F_1$ tissues: the immature tassel tissue, intercalary meristems and leaf bases, apical meristems, and immature ears are placed in an initiation medium which contain MS salts, supplemented with thiamine, agar, and sucrose. Cultures are incubated in the dark at about 23° C. All culture manipulations and selections are performed with the aid of a dissecting microscope.

After about 5 to 7 days, cellular outgrowths are observed from the surface of the explants. After about 7 to 21 days, the outgrowths are subcultured by placing them into fresh medium of the same composition. Some of the intact immature embryo explants are placed on fresh medium. Several subcultures later (after about 2 to 3 months) enough material is present from explants for subdivision of these embryogenic calli into two or more pieces.

Callus pieces from different explants are not mixed. After further growth and subculture (about 6 months after embryogenic callus initiation), there are usually between 1 and 100 pieces derived ultimately from each selected explant. During this time of culture expansion, a characteristic embryogenic culture morphology develops as a result of careful selection at each subculture. Any organized structures resembling roots or root primordia are discarded. Material known from experience to lack the capacity for sustained growth is also discarded (translucent, watery, embryogenic structures).

Structures with a firm consistency resembling at least in part the scutellum of the in vivo embryo are selected.

The callus is maintained on agar-solidified MS-type media. A preferred hormone is 2,4-D. Visual selection of embryo-like structures is done to obtain subcultures. Transfer of material other than that displaying embryogenic morphology results in loss of the ability to recover whole plants from the callus. Some calli exhibit somaclonal variation. These are phenotypic changes appearing in culture.

Cell suspensions are prepared from the calli by selecting cell populations that appear homogeneous macroscopically. A portion of the friable, rapidly growing embryogenic calli is inoculated into MS Medium. The calli in medium are incubated at about 27° C. on a gyrotary shaker in the dark or in the presence of low light. The resultant suspension culture is transferred about once every seven days by taking about 5 to 10 ml of the culture and introducing this inoculum into fresh medium of the composition listed above.

For regeneration, embryos which appear on the callus surface are selected and regenerated into whole plants by transferring the embryogenic structures into a sequence of solidified media which include decreasing concentrations of 2,4-D or other auxins. Other hormones which can be used in the media include dicamba, NAA, ABA, BAP, and 2-NCA. The reduction is relative to the concentration used in culture maintenance media. Plantlets are regenerated from these embryos by transfer to a hormone-free medium, subsequently transferred to soil, and grown to maturity.

Progeny are produced by taking pollen and selfing, backcrossing or sibling regenerated plants by methods well known to those skilled in the arts. Seeds are collected from the regenerated plants.

V. A PROCESS OF PREPARING A CORN PLANT AND A CORN PLANT PRODUCED BY THAT PROCESS

The present invention also provides a process of preparing a novel corn plant and a corn plant produced by such a process. In accordance with such a process, a first parent corn plant is crossed with a second parent corn plant wherein at least one of the first and second corn plants is inbred corn plant FBLL. In one embodiment, a corn plant prepared by such a process is a first generation $F_1$ hybrid corn plant prepared by a process wherein both the first and second parent corn plants are inbred corn plants.

Corn plants (*Zea mays* L.) can be crossed by either natural or mechanical techniques. Natural pollination occurs in corn when wind blows pollen from the tassels to the silks that protrude from the tops of the incipient ears. Mechanical pollination can be effected either by controlling the types of pollen that can blow onto the silks or by pollinating by hand.

In a preferred embodiment, crossing comprises the steps of:

(a) planting in pollinating proximity seeds of a first and a second parent corn plant;

(b) growing the seeds of the first and second parent corn plants into plants that bear flowers;

(c) emasculating flowers of either the first or second parent corn plant to produce an emasculated parent corn plant;

(d) allowing cross-pollination to occur between the first and second parent corn plant; and (e) harvesting seeds produced on the emasculated parent corn plant and growing the seed into a plant.

Parental plants are planted in pollinating proximity to each other by planting the parental plants in alternating rows, in blocks or in any other convenient planting pattern. Plants of both parental parents are cultivated and allowed to grow until the time of flowering. Advantageously, during this growth stage, plants are in general treated with fertilizer and/or other agricultural chemicals as considered appropriate by the grower.

At the time of flowering, in the event that plant FBLL is employed as the male parent, the tassels of the other parental plant are removed from all plants employed as the female parental plant. The detasseling can be achieved manually but also can be done by machine if desired.

The plants are then allowed to continue to grow and natural cross-pollination occurs as a result of the action of wind, which is normal in the pollination of grasses, including corn. As a result of the emasculation of the female parent plant, all the pollen from the male parent plant, e.g., FBLL, is available for pollination because tassels, and thereby pollen bearing flowering parts, have been previously removed from all plants of the inbred plant being used as the female in the hybridization. Of course, during this hybridization procedure, the parental varieties are grown such that they are isolated from other corn fields to prevent any accidental contamination of pollen from foreign sources. These isolation techniques are well within the skill of those skilled in this art.

Both of the parent inbred plants of corn are allowed to continue to grow until maturity, but only the ears from the female inbred parental plants are harvested to obtain seeds of a corn novel $F_1$ hybrid corn. The novel $F_1$ hybrid seed produced can then be planted in a subsequent growing season with the desirable characteristics in terms of $F_1$ hybrid corn plants providing improved grain yields and the other desirable characteristics disclosed herein, being achieved.

Alternatively, in another embodiment, both first and second parent corn plants can come from the same inbred corn plant FBLL. Thus, any corn plant produced using a process of the present invention and inbred corn plant FBLL is contemplated by this invention. As used herein, crossing can mean selfing, backcrossing, crossing to another or the same inbred, crossing to populations, and the like. All corn plants produced using inbred corn plant FBLL as a parent are within the scope of this invention.

The utility of inbred plant FBLL also extends to crosses with other species. Commonly, suitable species will be of the family Graminaceae, and especially of the genera Zea, Tripsacum, Coix, Schlerachne, Polytoca, Chionachne, and Trilobachne, of the tribe Maydeae. Of these, Zea and Tripsacum, are most preferred. Potentially suitable for crosses with FBLL can be the various varieties of grain sorghum, *Sorghum bicolor* (L.) Moench.

A. $F_1$ Hybrid Corn Plants and Seeds

Where inbred corn plant FBLL is crossed with another, different, corn inbred, a first generation ($F_1$) corn hybrid plant is produced. Both a $F_1$ hybrid corn plant and a seed of that $F_1$ hybrid corn plant are contemplated as aspects of the present invention. Inbred FBLL has been used to prepare an $F_1$ hybrid corn plant. Exemplary such hybrid corn plants are designated DK512, DK522, DK554, DK570, DK591, and DK623.

The goal of a process of producing an $F_1$ hybrid is to manipulate the genetic complement of corn to generate new combinations of genes which interact to yield new or improved traits (phenotypic characteristics). A process of producing an $F_1$ hybrid typically begins with the production of one or more inbred plants. Those plants are produced by repeated crossing of ancestrally related corn plants to try and concentrate certain genes within the inbred plants. The production of inbred FBLL has been set forth hereinbefore.

Corn has a diploid phase which means two conditions of a gene (two alleles) occupy each locus (position on a chromosome). If the alleles are the same at a locus, there is said to be homozygosity. If they are different, there is said to be heterozygosity. In a completely inbred plant, all loci are homozygous. Because many loci when homozygous are deleterious to the plant, in particular leading to reduced vigor, less kernels, weak and/or poor growth, production of inbred plants is an unpredictable and arduous process. Under some conditions, heterozygous advantage at some loci effectively bars perpetuation of homozygosity.

Inbreeding requires coddling and sophisticated manipulation by human breeders. Even in the extremely unlikely event inbreeding rather than crossbreeding occurred in natural corn, achievement of complete inbreeding cannot be expected in nature due to well known deleterious effects of homozygosity and the large number of generations the plant would have to breed in isolation. The reason for the breeder to create inbred plants is to have a known reservoir of genes whose gametic transmission is at least somewhat predictable.

The development of inbred plants generally requires at least about 5 to 7 generations of selfing. Inbred plants are then cross-bred in an attempt to develop improved $F_1$ hybrids. Hybrids are then screened and evaluated in small scale field trials. Typically, about 10 to 15 phenotypic traits, selected for their potential commercial value, are measured. A selection index of the most commercially important traits is used to help evaluate hybrids. FACT, an acronym for Field Analysis Comparison Trial (strip trials), is an on-farm testing program employed by to perform the final evaluation of the commercial potential of a product.

During the next several years, a progressive elimination of hybrids occurs based on more detailed evaluation of their phenotype. Eventually, strip trials (FACT) are conducted to formally compare the experimental hybrids being developed with other hybrids, some of which were previously developed and generally are commercially successful. That is, comparisons of experimental hybrids are made to competitive hybrids to determine if there was any advantage to further commercial development of the experimental hybrids. An example of such a comparison is presented below in Table 3.

Strip trials compare the phenotypes of hybrids grown in as many environments as possible and are performed in many environments to assess overall performance of the new hybrids and to select optimum growing conditions. Because the corn is grown in close proximity, environmental factors that affect gene expression, such as moisture, temperature, sunlight and pests, are minimized. For a decision to be made that a hybrid is worth making commercially available, it is not necessary that the hybrid be better than all other hybrids. Rather, significant improvements must be shown in at least some traits that would create improvements in some niches. Exemplary comparative data are set forth hereinafter for hybrids DK512, DK522, DK554, DK570, DK591, and DK623.

When the inbred parental plant FBLL is crossed with inbred plant MBSJ to yield hybrid DK570, FBLL can serve as either the maternal or paternal plant. For many crosses, the outcome is the same regardless of the assigned sex of the parental plants. However, there is often one of the parental plants that is preferred as the maternal plant because of increased seed yield and production characteristics. Some plants produce tighter ear husks leading to more loss, for example due to rot. There can be delays in silk formation which deleteriously affect timing of the reproductive cycle for a pair of parental inbreds. Seed coat characteristics can be preferable in one plant. Pollen can be shed better by one plant. Other variables can also affect preferred sexual assignment of a particular cross. In the production of DK512, DK522, DK554, DK570, DK591, and DK623, FBLL is preferred as the female parent, and the male parents used are the inbreds 3IIH6, 78551S, LIBC4, MBSJ, MBWZ, and MM501D, respectively (disclosed in U.S. patent application Ser. No. 08/186,264, filed Jan. 21, 1994; U.S. patent application Ser. No. 181,710, filed Jan. 14, 1994; U.S. patent application Ser. No. 08/165,001, filed Dec. 10, 1993; U.S. patent application Ser. No. 08/181,709, filed Jan. 14, 1994; U.S. patent application No. 08/175,109, filed Dec. 29, 1993; and U.S. patent application Ser. No. 08/180,911, filed Jan. 21, 1994 the disclosure of which is incorporated herein by reference).

MORPHOLOGICAL CHARACTERISTICS
OF CORN PLANT 78551S
YEAR OF DATA: 1988, 1989, 1990, 1991, and 1992

| CHARACTERISTIC | VALUE |
|---|---|
| 1. Stalk | |
| Diameter (Width) cm. | 2.4 |
| Nodes With Brace Roots | 1.2 |
| Internode Direction | STRAIGHT |
| Internode Length cm. | 14.2 |
| 2. Leaf | |
| Angle | INTERMEDIATE |
| Number | 17.6 |
| Color | MEDIUM GREEN |
| Length cm. | 72.6 |
| Width cm. | 9.5 |
| 3. Tassel | |
| Length cm. | 38.3 |
| Spike Length cm. | 30.2 |
| Peduncle Length cm. | 6.7 |
| Branch Number | 5.4 |
| Anther Color | GREEN-YELLOW |
| Glume Band | ABSENT |
| 4. Ear | |
| Silk Color | PINK |
| Number Per Stalk | 1.2 |
| Position (Attitude) | UPRIGHT |
| Length cm. | 17.8 |
| Diameter cm. | 3.8 |
| Weight gm. | 98.6 |
| Shank Length cm. | 13.3 |
| Shank Internodes | 6.5 |
| Husk Bract | SHORT |
| Husk Cover cm. | 6.6 |
| Husk Color Fresh | GREEN |
| Husk Color Dry | BUFF |
| Cob Diameter cm. | 2.2 |
| Cob Color | RED |
| Cob Strength | WEAK |
| Shelling Percent | 81.0 |
| 5. Kernel | |
| Row Number | 12.0 |
| Number Per Row | 27.7 |
| Cap Color | YELLOW |
| Side Color | ORANGE |
| Length (Depth) mm. | 10.2 |
| Width mm. | 8.8 |
| Thickness | 4.9 |
| Weight of 1000K gm. | 313.4 |
| Endosperm Type | NORMAL |
| Endosperm Color | YELLOW |

*These are typical values. Values may vary due to environment. Other values that are substantially equivalent are also within the scope of the invention. Substantially equivalent refers to quantitative traits that when compared do not show statistical differences of their means.

MORPHOLOGICAL TRAITS FOR
THE LIBC4 PHENOTYPE
YEAR OF DATA 1988, 1989, 1990, 1991, 1992

| CHARACTERISTIC | VALUE |
|---|---|
| 1. Stalk | |
| Diameter (Width) cm. | 2.2 |
| Anthocyanin | ABSENT |
| Nodes With Brace Roots | 1.2 |
| Internode Direction | STRAIGHT |
| Internode Length cm. | 15.0 |
| 2. Leaf | |
| Number | 17.3 |
| Color | MEDIUM GREEN |
| Length cm. | 69.8 |
| Width cm. | 9.5 |
| Marginal Waves | FEW |
| Longitudinal Creases | ABSENT |
| 3. Tassel | |
| Length cm. | 32.7 |
| Spike Length cm. | 23.8 |
| Peduncle Length cm. | 6.3 |
| Attitude | COMPACT |
| Branch Number | 4.5 |
| Anther Color | RED |
| Glume Color | GREEN |
| Glume Band | ABSENT |
| 4. Ear | |
| Silk Color | RED |
| Number Per Stalk | 1.2 |
| Position (Attitude) | UPRIGHT |
| Length cm. | 16.5 |
| Shape | SEMI-CONICAL |
| Diameter cm. | 3.7 |
| Weight gm. | 100.7 |
| Shank Length cm. | 13.8 |
| Shank Internode Number | 8.1 |
| Husk Bract | SHORT |
| Husk Cover cm. | 3.4 |
| Husk Opening | INTERMEDIATE |
| Husk Color Fresh | GREEN |
| Husk Color Dry | BUFF |
| Cob Diameter cm. | 2.2 |
| Cob Color | PINK |
| Shelling Percent | 83.1 |
| 5. Kernel | |
| Row Number | 14.4 |
| Number Per Row | 29.0 |
| Row Direction | CURVED |
| Type | DENT |
| Cap Color | YELLOW |
| Side Color | ORANGE |
| Length (Depth) mm. | 9.7 |
| Width mm. | 7.8 |
| Thickness | 4.8 |
| Weight of 1000K gm. | 251.6 |
| Endosperm Type | NORMAL |
| Endosperm Color | YELLOW |

MORPHOLOGICAL CHARACTERISTICS
OF CORN PLANT MBWZ
YEAR OF DATA 1990–1991

| CHARACTERISTIC | VALUE |
|---|---|
| 1. Stalk | |
| Diameter (Width) cm. | 2.2 |
| Anthocyanin | STRONG |
| Nodes With Brace Roots | 1.7 |
| Brace Root Color | GREEN |
| Internode Direction | STRAIGHT |
| Internode Length cm. | 14.9 |

-continued

MORPHOLOGICAL CHARACTERISTICS
OF CORN PLANT MBWZ
YEAR OF DATA 1990–1991

| CHARACTERISTIC | VALUE |
|---|---|
| 2. Leaf | |
| Angle | UPRIGHT |
| Number | 20.1 |
| Color | MEDIUM GREEN |
| Length cm. | 83.9 |
| Width cm. | 9.0 |
| Sheath Pubescence | LIGHT |
| Longitudinal Creases | ABSENT |
| 3. Tassel | |
| Length cm. | 32.6 |
| Spike Length cm. | 25.9 |
| Peduncle Length cm. | 9.1 |
| Attitude | COMPACT |
| Branch Angle | UPRIGHT |
| Branch Number | 4.8 |
| Anther Color | TAN |
| Glume Color | GREEN |
| Glume Band | ABSENT |
| 4. Ear | |
| Silk Color | PINK |
| Number Per Stalk | 1.4 |
| Position (Attitude) | UPRIGHT |
| Length cm. | 15.7 |
| Shape | SEMI-CONICAL |
| Diameter cm. | 4.0 |
| Weight gm. | 110.9 |
| Shank Length cm. | 10.2 |
| Shank Internodes | 7.9 |
| Husk Bract | SHORT |
| Husk Cover cm. | 6.3 |
| Husk Opening | INTERMEDIATE |
| Husk Color Fresh | GREEN |
| Husk Color Dry | BUFF |
| Cob Diameter cm. | 2.4 |
| Cob Color | RED |
| Cob Strength | WEAK |
| Shelling Percent | 82.6 |
| 5. Kernel | |
| Row Number | 15.7 |
| Number Per Row | 30.4 |
| Row Direction | CURVED |
| Type | DENT |
| Cap Color | YELLOW |
| Side Color | ORANGE |
| Length (Depth) mm. | 10.1 |
| Width mm. | 7.6 |
| Thickness | 4.4 |
| Weight of 1000K gm. | 244.5 |
| Endosperm Type | NORMAL |
| Endosperm Color | YELLOW |

MORPHOLOGICAL TRAITS FOR
THE MBSJ PHENOTYPE
YEAR OF DATA: 1987, 1988, 1989, 1990, 1991, and 1992
(Qualitative Traits)
YEAR OF DATA: 1989, 1990, 1991, and 1992 (Quantitative Traits)

| CHARACTERISTIC | VALUE |
|---|---|
| 1. Stalk | |
| Diameter (Width) cm. | 2.4 |
| Anthocyanin | ABSENT |
| Nodes With Brace Roots | 1.7 |
| Brace Root Color | GREEN |
| Internode Direction | STRAIGHT |
| Internode Length cm. | 14.4 |

MORPHOLOGICAL TRAITS FOR
THE MBSJ PHENOTYPE
YEAR OF DATA: 1987, 1988, 1989, 1990, 1991, and 1992
(Qualitative Traits)
YEAR OF DATA: 1989, 1990, 1991, and 1992 (Quantitative Traits)

| CHARACTERISTIC | VALUE |
|---|---|
| 2. Leaf | |
| Angle | INTERMEDIATE |
| Number | 16.8 |
| Color | MEDIUM GREEN |
| Length cm. | 70.4 |
| Width cm. | 8.3 |
| Sheath Anthocyanin | ABSENT |
| 3. Tassel | |
| Length cm. | 35.5 |
| Spike Length cm. | 27.8 |
| Peduncle Length cm. | 5.4 |
| Branch Angle | INTERMEDIATE |
| Branch Number | 6.6 |
| Anther Color | GREEN-YELLOW |
| Glume Color | GREEN |
| Glume Band | ABSENT |
| 4. Ear | |
| Silk Color | GREEN-YELLOW |
| Number Per Stalk | 1.0 |
| Position (Attitude) | UPRIGHT |
| Length cm. | 14.6 |
| Shape | SEMI-CONICAL |
| Diameter cm. | 3.7 |
| Weight gm. | 85.5 |
| Shank Length cm. | 12.8 |
| Shank Internode Number | 7.4 |
| Husk Bract | SHORT |
| Husk Cover cm. | 2.4 |

MORPHOLOGICAL TRAITS FOR
THE MBSJ PHENOTYPE
YEAR OF DATA: 1987, 1988, 1989, 1990, 1991, and 1992
(Qualitative Traits)
YEAR OF DATA: 1989, 1990, 1991, and 1992 (Quantitative Traits)

| CHARACTERISTIC | VALUE |
|---|---|
| Husk Color Fresh | GREEN |
| Husk Color Dry | BUFF |
| Cob Diameter cm. | 2.1 |
| Cob Color | WHITE |
| Cob Strength | WEAK |
| Shelling Percent | 82.9 |
| 5. Kernel | |
| Row Number | 14.5 |
| Number Per Row | 26.0 |
| Row Direction | CURVED |
| Type | DENT |
| Cap Color | YELLOW |
| Side Color | ORANGE |
| Length (Depth) mm. | 10.2 |
| Width mm. | 7.7 |
| Thickness | 4.4 |
| Weight of 1000 K gm. | 250.0 |
| Endosperm Type | NORMAL |
| Endosperm Color | YELLOW |

Table 3 presents a comparison of performance data for DK512, DK522, DK554, DK570, DK591, and DK623 versus selected hybrids of commercial value. These data represent results across years and locations for strip trials. The "NTEST" represents the number of paired observations in designated tests at locations around the United States.

TABLE 3

| Comparison | NTEST | SI % C | YLD BU | MST PTS | SV RAT | ELSTD % M | FGDU | PHT INCH | EHT INCH | BAR % | SG RAT | FLSTD % M | DRP % | STL % | RTL % | TST LBS | ESTR DAYS |
|---|---|---|---|---|---|---|---|---|---|---|---|---|---|---|---|---|---|
| COMPARATIVE DATA FOR DK512 | | | | | | | | | | | | | | | | | |
| DK512 | R 811 | 107.7 | 156.4 | 23.7 | 5.5 | 101.5 | 1254 | 90.3 | 43.0 | 0.5 | 5.0 | 100.0 | 0.0 | 4.2 | 0.5 | 51.7 | 99.7 |
| DK485 | | 99.4 | 147.5 | 23.5 | 5.5 | 98.0 | 1242 | 85.5 | 38.9 | 0.2 | 4.6 | 99.8 | 0.1 | 3.1 | 0.8 | 51.7 | 99.1 |
| | | ** | ** | + | | ** | ** | ** | ** | + | * | | | ** | ** | | |
| | F405 | 108.4 | 149.5 | 22.5 | | | | | | | | 101.2 | 0.2 | 3.7 | 0.7 | 52.2 | 99.3 |
| | | 102.5 | 141.8 | 22.2 | | | | | | | | 98.2 | 0.2 | 2.1 | 0.6 | 52.7 | 98.9 |
| | | ** | ** | ** | | | | | | | | ** | ** | ** | * | | ** |
| DK512 | R 558 | 109.3 | 158.7 | 23.2 | 5.5 | 103.0 | 1289 | 89.2 | 41.4 | 0.6 | 4.9 | 100.2 | 0.1 | 3.0 | 0.6 | 51.3 | 99.6 |
| DK501 | | 97.7 | 148.2 | 24.1 | 5.4 | 100.4 | 1279 | 82.7 | 32.2 | 0.7 | 3.4 | 100.0 | 0.1 | 1.6 | 1.3 | 50.8 | 100.2 |
| | | ** | ** | ** | | * | | ** | ** | | ** | + | | ** | ** | | |
| | F 343 | 110.1 | 154.6 | 20.7 | | | | | | | | 101.3 | 0.2 | 3.9 | 0.7 | 52.8 | 99.3 |
| | | 99.6 | 144.6 | 21.9 | | | | | | | | 100.3 | 0.1 | 1.6 | 0.6 | 52.7 | 100.7 |
| | | ** | ** | ** | | | | | | | | + | * | ** | | | |
| DK512 | R 561 | 110.4 | 165.6 | 22.9 | 5.4 | 101.2 | 1253 | 90.4 | 42.7 | 0.4 | 4.7 | 100.2 | 0.1 | 5.4 | 0.5 | 52.5 | 100.1 |
| DK535 | | 91.6 | 150.3 | 25.5 | 5.1 | 98.1 | 1260 | 88.0 | 38.9 | 0.4 | 4.8 | 100.1 | 0.1 | 2.5 | 1.1 | 52.5 | 102.9 |
| | | ** | ** | ** | ** | * | | ** | ** | | | | | ** | ** | | |
| | F 393 | 111.0 | 154.6 | 19.9 | | | | | | | | 100.6 | 0.1 | 4.0 | 0.7 | 53.4 | 99.9 |
| | | 95.0 | 142.4 | 22.4 | | | | | | | | 101.7 | 0.2 | 1.5 | 1.6 | 53.6 | 103.2 |
| | | ** | ** | ** | | | | | | | | * | + | ** | * | * | ** |
| DK512 | R 66 | 108.8 | 157.7 | 20.3 | 5.3 | 103.8 | 1332 | 85.6 | 38.9 | 0.2 | 4.4 | 101.1 | 0.2 | 11.1 | 1.6 | 56.1 | 100.2 |
| DK547 | | 93.5 | 147.1 | 23.0 | 5.6 | 106.0 | 1354 | 84.2 | 38.1 | 0.2 | 5.0 | 100.6 | 0.2 | 9.4 | 2.6 | 56.2 | 102.8 |
| | | ** | ** | ** | + | + | * | | | | * | | | + | | | |
| | F 182 | 113.0 | 166.9 | 20.2 | | | | | | | | 102.2 | 0.2 | 3.5 | 0.5 | 53.0 | 99.8 |
| | | 98.4 | 156.6 | 22.9 | | | | | | | | 102.0 | 0.2 | 1.6 | 0.8 | 53.7 | 103.3 |
| | | ** | ** | ** | | | | | | | | | | ** | | | ** |
| COMPARATIVE DATA FOR DK522 | | | | | | | | | | | | | | | | | |
| DK522 | R 1054 | 102.4 | 153.2 | 22.1 | 5.4 | 100.3 | 1297 | 87.6 | 37.1 | 1.2 | 4.7 | 100.3 | 0.1 | 4.0 | 0.7 | 53.9 | 101.7 |
| DK485 | | 99.9 | 146.7 | 19.8 | 5.6 | 93.5 | 1289 | 83.8 | 38.2 | 0.9 | 3.9 | 98.8 | 0.2 | 4.3 | 1.2 | 53.7 | 99.2 |
| | | ** | ** | ** | ** | ** | ** | ** | ** | + | ** | ** | | * | ** | * | ** |

TABLE 3-continued

| Compari-son | NTEST | SI % C | YLD BU | MST PTS | SV RAT | ELSTD % M | FGDU | PHT INCH | EHT INCH | BAR % | SG RAT | FLSTD % M | DRP % | STL % | RTL % | TST LBS | ESTR DAYS |
|---|---|---|---|---|---|---|---|---|---|---|---|---|---|---|---|---|---|
|  | F 221 | 100.2 | 139.0 | 20.9 |  |  |  |  |  |  |  | 98.5 | 0.3 | 3.3 | 0.4 | 53.1 | 101.6 |
|  |  | 101.4 | 136.0 | 18.6 |  |  |  |  |  |  |  | 98.2 | 0.2 | 3.6 | 0.7 | 53.9 | 98.2 |
|  |  |  | ** | ** |  |  |  |  |  |  |  |  |  |  | + |  | ** |
| DK522 | R 287 | 111.9 | 153.8 | 20.6 | 5.3 | 98.9 | 1327 | 89.3 | 38.5 | 2.0 | 4.9 | 100.2 | 0.3 | 3.6 | 0.6 | 52.2 | 101.2 |
| DK524 |  | 97.6 | 142.8 | 20.3 | 5.7 | 103.3 | 1348 | 90.1 | 44.4 | 1.4 | 4.8 | 100.3 | 0.6 | 6.2 | 2.7 | 53.9 | 100.9 |
|  |  | ** | ** | * | ** | ** | ** | * | ** |  |  |  | ** | ** | ** | ** |  |
|  | F 142 | 100.8 | 132.7 | 20.4 |  |  |  |  |  |  |  | 99.5 | 0.1 | 3.2 | 0.2 | 53.8 | 101.8 |
|  |  | 95.3 | 128.5 | 20.1 |  |  |  |  |  |  |  | 98.3 | 0.3 | 5.0 | 1.0 | 55.4 | 101.2 |
|  |  | ** | ** | + |  |  |  |  |  |  |  | * | ** | ** | ** | ** |  |
| COMPARATIVE DATA FOR DK554 |||||||||||||||||
| DK554 | R 1368 | 101.4 | 152.8 | 19.5 | 5.1 | 101.3 | 1312 | 84.7 | 38.9 | 0.8 | 4.5 | 100.2 | 0.1 | 4.5 | 0.5 | 54.1 | 104.2 |
| DK535 |  | 99.3 | 150.4 | 19.8 | 5.5 | 100.1 | 1292 | 84.8 | 38.5 | 1.3 | 3.4 | 100.3 | 0.3 | 2.6 | 1.5 | 55.2 | 104.4 |
|  |  | ** | ** | ** | ** | ** | ** |  | ** | ** | ** |  | ** | ** | ** | ** |  |
|  | F 905 | 104.9 | 148.7 | 19.9 |  |  |  |  |  |  |  | 99.3 | 0.2 | 2.6 | 0.2 | 54.2 | 103.9 |
|  |  | 99.2 | 142.9 | 19.7 |  |  |  |  |  |  |  | 101.4 | 0.4 | 2.1 | 1.1 | 54.9 | 103.5 |
|  |  | ** | ** | ** |  |  |  |  |  |  |  | ** | ** | ** | ** | ** |  |
| DK554 | R 617 | 103.7 | 144.3 | 17.9 | 5.0 | 100.4 | 1361 | 81.7 | 37.7 | 1.1 | 4.3 | 100.3 | 0.1 | 5.2 | 0.6 | 54.9 | 103.9 |
| DK547 |  | 95.6 | 137.6 | 18.6 | 5.7 | 102.7 | 1351 | 83.4 | 39.3 | 1.5 | 3.9 | 100.4 | 0.4 | 4.4 | 1.4 | 56.4 | 104.6 |
|  |  | ** | ** | ** | ** | ** | ** | ** | ** | * | ** |  | ** | ** | ** | ** |  |
|  | F 445 | 105.6 | 153.8 | 20.3 |  |  |  |  |  |  |  | 99.9 | 0.3 | 3.1 | 0.3 | 53.8 | 103.6 |
|  |  | 99.6 | 148.7 | 20.6 |  |  |  |  |  |  |  | 101.5 | 0.5 | 3.0 | 0.7 | 55.0 | 104.1 |
|  |  | ** | ** | ** |  |  |  |  |  |  |  | ** | ** |  | * | ** |  |
| DK554 | R 710 | 103.6 | 144.6 | 17.8 | 5.0 | 100.3 | 1363 | 81.8 | 37.7 | 1.0 | 4.3 | 100.3 | 0.1 | 5.3 | 0.6 | 54.6 | 103.9 |
| DK584 |  | 97.1 | 140.8 | 19.5 | 5.3 | 105.3 | 1350 | 77.9 | 32.2 | 1.8 | 3.5 | 100.9 | 0.2 | 3.9 | 1.0 | 55.9 | 106.1 |
|  |  | ** | ** | ** | ** | ** | ** | ** | ** | ** | ** | ** | * | ** | ** | ** | ** |
|  | F 463 | 108.1 | 148.3 | 18.7 |  |  |  |  |  |  |  | 99.5 | 0.2 | 2.4 | 0.4 | 54.7 | 104.4 |
|  |  | 95.9 | 139.8 | 20.0 |  |  |  |  |  |  |  | 102.5 | 0.4 | 3.0 | 1.3 | 55.7 | 106.7 |
|  |  | ** | ** | ** |  |  |  |  |  |  |  | ** | ** | ** | ** | ** | ** |
| COMPARATIVE DATA FOR DK570 |||||||||||||||||
| DK570 | R864 | 98.2 | 140.3 | 19.5 | 5.3 | 100.4 | 1321 | 86.8 | 34.6 | 2.8 | 4.4 | 100.3 | 0.2 | 3.3 | 1.1 | 55.2 | 105.8 |
| DK547 |  | 96.0 | 137.5 | 18.5 | 5.7 | 101.6 | 1339 | 84.0 | 39.9 | 1.8 | 4.0 | 100.3 | 0.3 | 4.5 | 1.8 | 56.1 | 104.5 |
|  |  | ** | ** | ** | ** | ** | ** | ** | ** | ** | ** |  | ** | ** | ** | * |  |
|  | F 545 | 101.2 | 142.3 | 19.8 |  |  |  |  |  |  |  | 100.4 | 0.4 | 2.8 | 0.3 | 54.7 | 106.3 |
|  |  | 100.1 | 140.3 | 18.7 |  |  |  |  |  |  |  | 101.8 | 0.6 | 3.9 | 0.6 | 55.7 | 104.4 |
|  |  | + | ** | ** |  |  |  |  |  |  |  | ** | ** | ** | ** | ** | ** |
| DK570 | R 114 | 105.8 | 135.0 | 18.9 | 5.7 | 101.3 | 1331 | 82.3 | 32.8 | 3.1 | 4.5 | 100.6 | 0.1 | 3.5 | 2.0 | 57.7 | 105.2 |
| DK572 |  | 95.2 | 127.7 | 19.3 | 5.8 | 102.7 | 1397 | 78.7 | 39.9 | 4.4 | 4.4 | 100.8 | 0.4 | 6.0 | 2.6 | 58.8 | 106.1 |
|  |  | ** | ** | ** |  |  | ** | ** | ** |  |  |  | ** | ** |  | ** |  |
|  | F 238 | 102.5 | 143.5 | 19.1 |  |  |  |  |  |  |  | 100.7 | 0.3 | 2.5 | 0.3 | 55.1 | 106.9 |
|  |  | 93.9 | 137.2 | 18.7 |  |  |  |  |  |  |  | 100.1 | 0.8 | 5.6 | 0.7 | 56.8 | 106.0 |
|  |  | ** | ** | ** |  |  |  |  |  |  |  |  | ** | ** | * | ** |  |
| COMPARATIVE DATA FOR DK591 |||||||||||||||||
| DK591 | R 246 | 111.9 | 157.0 | 19.7 | 5.4 | 100.1 | 1402 | 90.9 | 43.1 | 1.2 | 5.7 | 100.4 | 0.2 | 6.0 | 1.1 | 54.4 | 107.7 |
| DK584 |  | 94.0 | 137.7 | 19.2 | 5.5 | 103.3 | 1343 | 78.5 | 32.8 | 1.0 | 3.2 | 100.5 | 0.1 | 5.4 | 1.2 | 55.3 | 107.6 |
|  |  | ** | ** | ** |  | ** | ** | ** | ** |  | ** |  |  |  |  |  | * |
|  | F 135 | 108.6 | 172.4 | 21.8 |  |  |  |  |  |  |  | 102.4 | 0.0 | 1.5 | 1.6 | 54.2 | 108.9 |
|  |  | 91.0 | 152.5 | 20.4 |  |  |  |  |  |  |  | 101.1 | 0.1 | 1.4 | 2.4 | 55.7 | 107.5 |
|  |  | ** | ** | ** |  |  |  |  |  |  |  | * |  |  | + | ** |  |
| DK591 | R 721 | 107.4 | 174.3 | 18.6 | 5.7 | 100.2 | 1326 | 90.8 | 43.0 | 1.0 | 4.5 | 100.2 | 0.1 | 3.1 | 2.0 | 57.8 | 109.0 |
| DK612 |  | 82.5 | 151.8 | 20.0 | 5.7 | 97.9 | 1271 | 78.3 | 33.5 | 1.4 | 4.1 | 100.2 | 0.1 | 2.2 | 2.4 | 58.9 | 110.9 |
|  |  | ** | ** | ** |  | ** | ** | ** | ** | * | ** |  |  |  | + | ** | ** |
|  | F 267 | 108.7 | 177.0 | 21.5 |  |  |  |  |  |  |  | 102.7 | 0.1 | 3.0 | 1.3 | 54.0 | 108.8 |
|  |  | 92.4 | 161.7 | 22.1 |  |  |  |  |  |  |  | 100.4 | 0.1 | 2.0 | 2.1 | 55.7 | 110.1 |
|  |  | ** | ** | ** |  |  |  |  |  |  |  | ** |  |  | + | ** |  |
| DK591 | R 239 | 111.1 | 167.3 | 17.8 | 5.5 | 99.3 | 1358 | 90.4 | 42.7 | 1.3 | 4.3 | 100.0 | 0.1 | 3.6 | 0.5 | 57.8 | 108.8 |
| DK614 |  | 96.7 | 156.4 | 19.6 | 5.5 | 100.1 | 1346 | 86.5 | 39.7 | 2.2 | 4.3 | 100.1 | 0.2 | 3.0 | 0.7 | 59.3 | 110.9 |
|  |  | ** | ** | ** |  |  | ** | ** | ** | * |  |  | ** | * | * | ** |  |
|  | F 150 | 107.4 | 160.4 | 21.9 |  |  |  |  |  |  |  | 100.3 | 0.0 | 3.6 | 1.1 | 54.1 | 108.2 |
|  |  | 99.7 | 155.3 | 23.5 |  |  |  |  |  |  |  | 101.5 | 0.0 | 3.3 | 0.8 | 55.2 | 110.4 |
|  |  | ** | ** | ** |  |  |  |  |  |  |  |  |  |  |  | ** |  |
| COMPARATIVE DATA FOR DK623 |||||||||||||||||
| DK623 | R 508 | 97.7 | 175.0 | 21.6 | 5.7 | 98.3 | 1305 | 88.7 | 36.5 | 2.2 | 4.4 | 100.1 | 0.1 | 3.2 | 1.2 | 58.7 | 111.1 |
| DK612 |  | 81.0 | 157.9 | 21.0 | 5.7 | 97.6 | 1251 | 79.9 | 34.0 | 0.8 | 4.2 | 100.2 | 0.0 | 2.2 | 3.2 | 58.7 | 110.8 |
|  |  | ** | ** | ** |  |  | ** | ** | ** | ** | * |  | * | ** | ** |  |  |
|  | F 344 | 102.0 | 164.1 | 21.2 |  |  |  |  |  |  |  | 101.0 | 0.2 | 3.8 | 0.6 | 55.7 | 111.0 |
|  |  | 94.6 | 155.3 | 20.7 |  |  |  |  |  |  |  | 100.7 | 0.2 | 2.1 | 2.0 | 56.5 | 110.3 |
|  |  | ** | ** | ** |  |  |  |  |  |  |  |  |  | ** | ** | ** |  |
| DK623 | R 357 | 97.5 | 172.1 | 19.9 | 5.8 | 97.4 | 1340 | 90.0 | 36.5 | 3.2 | 4.3 | 99.9 | 0.1 | 3.2 | 0.6 | 58.9 | 111.6 |
| DK636 |  | 91.7 | 169.4 | 21.3 | 5.4 | 98.3 | 1366 | 91.2 | 41.8 | 2.5 | 4.0 | 99.9 | 0.1 | 2.5 | 2.0 | 60.0 | 113.4 |
|  |  | ** | ** | ** | ** | ** | ** |  | ** | + | + |  |  | ** | ** | ** |  |
|  | F 429 | 106.2 | 162.8 | 19.9 |  |  |  |  |  |  |  | 101.0 | 0.1 | 3.5 | 0.4 | 56.9 | 111.2 |
|  |  | 97.2 | 156.5 | 21.1 |  |  |  |  |  |  |  | 101.0 | 0.1 | 2.9 | 1.2 | 57.2 | 113.2 |

TABLE 3-continued

| Compari-son | NTEST | SI % C | YLD BU | MST PTS | SV RAT | ELSTD % M | FGDU | PHT INCH | EHT INCH | BAR % | SG RAT | FLSTD % M | DRP % | STL % | RTL % | TST LBS | ESTR DAYS |
|---|---|---|---|---|---|---|---|---|---|---|---|---|---|---|---|---|---|
| | | ** | ** | ** | | | | | | | | | | * | ** | ** | |

Legend Abbreviations
SI % C = Selection Index (Percent of Check)
YLD BU = Yield (Bushels/Acre)
MST PTS = Moisture
SV RAT = Seedling Vigor Rating
ELSTD % M = Early Stand (Percent of Test Mean)
FGDU = GDUs to Shed
PHT INCH = Plant Height (Inches)
EHT INCH = Ear Height (Inches)
BAR % = Barren Plants (Percent)
SG RAT = Staygreen Rating
FLSTD % M = Final Stand (Percent of Test Mean)
DRP % = Dropped Ears (Percent)
STL % = Stalk Lodging (Percent)
RTL % = Root Lodging (Percent)
TST LBS = Test Weight (Pounds)
ESTR DAYS = Estimated Relative Maturity (Days)
Significance levels are indicated as:
+ = 10 percent
* = 5 percent
** = 1 percent As can be seen in Table 3, hybrids that contain FBLL have significant differences from other commercial hybrids.

For example, when comparing DK512 to DK485 in research testing, DK512 has significantly higher selection index, higher yield, higher moisture, higher early stand, later flowering, higher plant height, higher ear height, higher barren plants, higher staygreen rating, higher final stand, higher stalk lodging, and lower root lodging. In comparing DK512 to DK485 in FACT testing, DK512 has significantly higher selection index, higher yield, higher moisture, higher final stand, higher stalk lodging, and lower test weight. Comparing DK512 to DK501 in research testing, DK512 has significantly higher selection index, higher yield, lower moisture, higher early stand, higher plant height, higher ear height, higher staygreen rating, higher final stand, higher stalk lodging, and lower root lodging. Compared to DK501 in FACT testing, DK512 has significantly higher selection index, higher yield, lower moisture, higher final stand, higher dropped ears, and higher stalk lodging. In comparing DK512 to DK535 in research testing, DK512 has significantly higher selection index, higher yield, lower moisture, higher seedling vigor, higher early stand, earlier flowering, higher plant height, higher ear height, higher stalk lodging, and lower root lodging. Comparing DK512 to DK535 in FACT testing, DK512 has significantly higher selection index, higher yield, lower moisture, lower final stand, lower dropped ears, higher stalk lodging, lower root lodging, and lower test weight. Comparing DK512 to DK547 in research testing, DK512 has significantly higher selection index, higher yield, lower moisture, lower seedling vigor, lower early stand, earlier flowering, lower staygreen rating, and higher stalk lodging. In comparing DK512 to DK547 in FACT testing, DK512 has significantly higher selection index, higher yield, lower moisture, higher stalk lodging, and lower test weight.

Comparing DK522 to DK485 in research testing, DK522 has significantly higher selection index, higher yield, higher moisture, lower seedling vigor, higher early stand, later flowering, higher plant height, lower ear height, higher barren plants, higher staygreen rating, higher final stand, lower dropped ears, lower stalk lodging, and lower root lodging. In comparing DK522 to DK485 in FACT testing, DK522 has significantly higher yield, higher moisture, lower root lodging, and lower test weight. In comparing DK522 to DK524 in research testing, DK522 has significantly higher selection index, higher yield, higher moisture, lower seedling vigor, lower early stand, earlier flowering, lower plant height, lower ear height, lower dropped ears, lower stalk lodging, lower root lodging, and lower test weight. In comparing DK522 to DK524 in FACT testing, DK522 has significantly higher selection index, higher yield, higher moisture, lower dropped ears, lower stalk lodging, lower root lodging, and lower test weight.

Comparing DK554 to DK535 in research testing, DK554 has significantly higher selection index, higher yield, lower moisture, lower seedling vigor, higher early stand, later flowering, higher ear height, lower barren plants, higher staygreen rating, lower dropped ears, higher stalk lodging, lower root lodging, and lower test weight. Compared to DK535 in FACT testing, DK554 has significantly higher selection index, higher yield, higher moisture, lower final stand, lower ear droppage, higher stalk lodging, lower root lodging, and lower test weight. Comparing DK554 to DK547 in research testing, DK554 has significantly higher selection index, higher yield, lower moisture, lower seedling vigor, lower early stand, later flowering, lower plant height, lower ear height, lower barren plants, higher staygreen rating, lower ear droppage, higher stalk lodging, lower root lodging, and lower test weight. Compared to DK547 in FACT testing, DK554 has significantly higher selection index, higher yield, lower moisture, lower final stand, lower dropped ears, lower root lodging, and lower test weight. Comparing DK554 to DK584 in research testing, DK554 has significantly higher selection index, higher yield, lower moisture, lower seedling vigor, lower early stand, later flowering, higher plant height, higher ear height, lower barren plants, higher staygreen rating, lower final stand, lower dropped ears, higher stalk lodging, lower root lodging, and lower test weight. Comparing DK554 to DK584 in FACT testing, DK554 has significantly higher selection index, higher yield, lower moisture, lower final stand, lower dropped ears, lower stalk lodging, lower root lodging, and lower test weight.

Compared to DK547 in research testing, DK570 has significantly higher selection index, higher yield, higher moisture, lower seedling vigor rating, lower early stand, early flowering, higher plant height, lower ear height, higher barren plants, higher staygreen rating, lower ear droppage, lower stalk lodging, lower root lodging, and lower test weight. Compared to DK547 in FACT testing, DK570 has significantly higher selection index, higher yield, higher moisture, lower final stand, lower ear droppage, lower stalk lodging, and lower test weight. Comparing DK570 to DK572 in research testing, DK570 has significantly higher selection index, higher yield, lower moisture, earlier flowering, higher plant height, lower ear height, lower ear droppage, and lower stalk lodging. Compared to DK572 in FACT testing, DK570 has significantly higher selection index, higher yield, higher moisture, lower ear droppage, lower stalk lodging, lower root lodging, and lower test weight.

In comparing DK591 to DK584 in research testing, DK591 has significantly higher selection index, higher yield, higher moisture, lower early stand, later flowering, higher plant height, higher ear height, higher staygreen rating, and lower test weight. In comparing DK591 to DK584 in FACT testing, DK591 has significantly higher selection index, higher yield, higher moisture, lower ear droppage, lower root lodging, and lower test weight. In comparing DK591 to DK612 in research testing, DK591 has significantly higher selection index, higher yield, lower moisture, higher early stand, later flowering, higher plant height, higher ear height, lower barren plants, higher staygreen rating, higher stalk lodging, lower root lodging, and lower test weight. In comparing DK591 to DK612 in FACT testing, DK591 has significantly higher selection index, higher yield, lower moisture, higher final stand, higher stalk lodging, lower root lodging, and lower test weight. In comparing DK591 to DK614 in research testing, DK591 has significantly higher selection index, higher yield, lower moisture, later flowering, higher plant height, higher ear height, lower barren plants, lower dropped ears, higher stalk lodging, and lower test weight. In comparing DK591 to DK614 in FACT testing, DK591 has significantly higher selection index, higher yield, lower moisture, and lower test weight.

When comparing DK623 to DK612 in research tests, DK623 has significantly higher selection index, higher yield, higher moisture, later flowering, higher plant height, higher ear height, higher barren plants, higher staygreen rating, higher ear droppage, higher stalk lodging, and lower root lodging. In FACT testing, DK623 has significantly higher selection index, higher yield, higher moisture, higher stalk lodging, lower root lodging, and lower test weight, compared to DK612. In comparing DK623 to DK636 in research testing, DK623 has significantly higher selection index, higher yield, lower moisture, higher seedling vigor, earlier flowering, lower plant height, lower ear height, higher barren plants, higher staygreen, higher stalk lodging, lower root lodging and lower test weight. In comparing DK623 to DK636 in FACT testing, DK623 has significantly higher selection index, higher yield, lower moisture, higher stalk lodging, lower root lodging, and lower test weight.

As can be seen from this summary, hybrids that contain FBLL as one of the parents differ significantly from commercial hybrids currently in the marketplace.

Physical Description of $F_1$ Hybrid

The present invention contemplates an $F_1$ hybrid corn plant derived from corn plant FBLL. Physical characteristics of an exemplary such hybrid are set forth below in Table 4. An explanation of terms used in Table 4 can be found in the Definitions, set forth hereinbefore.

TABLE 4

MORPHOLOGICAL TRAITS FOR
THE DK512, DK522, DK554, DK570, DK591, and DK623 PHENOTYPES
YEAR OF DATA: 1989, 1990, 1991, and 1992

| CHARACTERISTIC | DKB12 | DK522 | DK554 | DK570 | DK591 | DK623 |
|---|---|---|---|---|---|---|
| 1. Stalk | | | | | | |
| Diameter (Width) cm. | 2.4 | 2.4 | 2.3 | 2.4 | 2.4 | 2.6 |
| Anthocyanin | ABSENT | — | ABSENT | ABSENT | — | ABSENT |
| Nodes w/Brace Roots | 1.5 | 1.5 | 1.6 | 1.5 | 1.9 | 2.2 |
| Brace Root Color | — | — | GREEN | GREEN | GREEN | GREEN |
| Internode Direction | STRAIGHT | STRAIGHT | STRAIGHT | STRAIGHT | STRAIGHT | STRAIGHT |
| Internode Length cm. | 16.0 | 16.8 | 19.2 | 18.9 | 19.1 | 18.4 |
| 2. Leaf | | | | | | |
| Angle | — | INTERMEDIATE | INTERMEDIATE | INTERMEDIATE | — | — |
| Number | 19.2 | 19.3 | 18.8 | 19.1 | 20.2 | 19.6 |
| Color | DK GREEN | DK GREEN | DK GREEN | DK GREEN | DK GREEN | DK GREEN |
| Length cm. | 82.4 | 91.4 | 84.3 | 86.7 | 88.4 | 89.5 |
| Width cm. | 9.5 | 10.4 | 10.0 | 9.2 | 9.7 | 10.9 |
| Sheath Anthocyanin | ABSENT | — | ABSENT | ABSENT | — | ABSENT |
| Marginal Waves | FEW | — | FEW | MANY | FEW | FEW |
| 3. Tassel | | | | | | |
| Length cm. | 37.3 | 42.2 | 36.8 | 39.7 | 35.1 | 34.1 |
| Spike Length cm. | 27.6 | 29.5 | 26.8 | 28.9 | 25.9 | 25.2 |
| Peduncle Length cm. | 11.6 | 8.8 | 11.6 | 11.9 | 12.1 | 8.5 |
| Attitude | OPEN | — | COMPACT | — | COMPACT | COMPACT |
| Branch Angle | — | — | — | INTERMEDIATE | — | UPRIGHT |
| Branch Number | 9.7 | 6.9 | 6.5 | 7.1 | 7.9 | 7.2 |
| Anther Color | — | GRN-YELLOW | — | — | PINK | GRN-YELLOW |
| Glume Color | GREEN | GREEN | GREEN | GREEN | GREEN | GREEN |
| Glume Band | ABSENT | ABSENT | ABSENT | ABSENT | ABSENT | ABSENT |

TABLE 4-continued

MORPHOLOGICAL TRAITS FOR
THE DK512, DK522, DK554, DK570, DK591, and DK623 PHENOTYPES
YEAR OF DATA: 1989, 1990, 1991, and 1992

| CHARACTERISTIC | DKB12 | DK522 | DK554 | DK570 | DK591 | DK623 |
|---|---|---|---|---|---|---|
| 4. Ear | | | | | | |
| Silk Color | — | GRN-YELLOW | — | GRN-YELLOW | — | GRN-YELLOW |
| Number Per Stalk | 1.1 | 1.1 | 1.1 | 1.2 | 1.0 | 1.1 |
| Position (Attitude) | UPRIGHT | UPRIGHT | UPRIGHT | UPRIGHT | UPRIGHT | UPRIGHT |
| Length cm. | 18.3 | 22.3 | 19.9 | 18.2 | 18.6 | 18.3 |
| Shape | SEMI-CONICAL | SEMI-CONICAL | SEMI-CONICAL | SEMI-CONICAL | SEMI-CONICAL | SEMI-CONICAL |
| Diameter cm. | 4.7 | 4.7 | 4.5 | 4.7 | 4.6 | 4.8 |
| Weight gm. | 222.2 | 247.1 | 213.0 | 196.5 | 218.5 | 256.6 |
| Shank Length cm. | 12.4 | 15.0 | 15.5 | 12.5 | 11.7 | 12.6 |
| Shank Internodes | 6.2 | 6.8 | 7.2 | 7.2 | 7.5 | 7.5 |
| Husk Bract | SHORT | SHORT | SHORT | SHORT | SHORT | SHORT |
| Husk Cover cm. | 0.9 | 2.2 | 1.5 | 1.9 | 3.0 | 2.1 |
| Husk Opening | OPEN | — | — | — | — | OPEN |
| Husk Color Fresh | GREEN | — | GREEN. | — | GREEN | GREEN |
| Husk Color Dry | BUFF | BUFF | BUFF | BUFF | BUFF | BUFF |
| Cob Diameter cm. | 2.6 | 2.5 | 2.5 | 2.5 | 2.5 | 2.6 |
| Cob Color | RED | RED | RED | RED | RED | RED |
| Cob Strength | STRONG | WEAK | STRONG | — | STRONG | — |
| Shelling Percent | 88.1 | 87.1 | 87.3 | 86.3 | 87.1 | 88.5 |
| 5. Kernel | | | | | | |
| Row Number | 18.2 | 15.1 | 16.6 | 17.9 | 17.4 | 19.1 |
| Number Per Row | 39.1 | 45.6 | 41.5 | 39.5 | 39.9 | 40.3 |
| Row Direction | CURVED | CURVED | CURVED | CURVED | CURVED | CURVED |
| Type | DENT | DENT | DENT | DENT | DENT | DENT |
| Cap Color | YELLOW | — | YELLOW | YELLOW | YELLOW | YELLOW |
| Side Color | DEEP YELLOW | — | ORANGE | — | — | ORANGE |
| Length (Depth) mm. | 13.8 | 12.9 | 12.4 | 13.2 | 12.9 | 13.6 |
| Width mm. | 7.6 | 8.7 | 8.0 | 7.5 | 7.8 | 7.5 |
| Thickness | 4.5 | 4.3 | 4.1 | 4.1 | 4.0 | 4.2 |
| Weight of 1000 K gm. | 318.3 | 336.2 | 301.8 | 299.2 | 298.8 | 319.8 |
| Endosperm Type | NORMAL | NORMAL | NORMAL | NORMAL | NORMAL | NORMAL |
| Endosperm Color | YELLOW | YELLOW | YELLOW | YELLOW | YELLOW | YELLOW |

*These are typical values. Values may vary due to environment. Other values that are substantially equivalent are also within the scope of the invention. Substantially equivalent refers to quantitative traits that when compared do not show statistical difference of their means.

VI. GENETIC COMPLEMENTS

In another aspect, the present invention provides a genetic complement of a plant of this invention. In one embodiment, therefore, the present invention contemplates an inbred genetic complement of inbred corn plant FBLL. In another embodiment, the present invention contemplates a hybrid genetic complement formed by the combination of a haploid genetic complement from FBLL and another haploid genetic complement.

As used herein, the phrase "genetic complement" means an aggregate of nucleotide sequences, the expression of which sequences defines the phenotype of a corn plant or a cell or tissue of that plant. Means for determining a genetic complement are well-known in the art. By way of example, a corn plant is genotyped to determine the array of the inherited markers it possesses. Markers are alleles at a single locus. They are preferably inherited in codominant fashion so that the presence of both alleles at a diploid locus is readily detectable, and they are free of environmental variation, i.e., their heritability is 1. This genotyping is preferably performed on at least one generation of the descendant plant for which the numerical value of the quantitative trait or traits of interest are also determined. The array of single locus genotypes is expressed as a profile of marker alleles, two at each locus. The marker allelic composition of each locus can be either homozygous or heterozygous. Homozygosity is a condition where both alleles at a locus are characterized by the same nucleotide sequence. Heterozygosity refers to different conditions of the gene at a locus. Markers that are used for purposes of this invention include restriction fragment length polymorphisms (RFLPs) and isozymes.

A plant genetic complement can be defined by a genetic marker profile that can be considered "fingerprints" of a genetic complement. For purposes of this invention, markers are preferably distributed evenly throughout the genome to increase the likelihood they will be near a quantitative trait loci (QTL) of interest (e.g., in tomatoes, Nienhuis, et al. 1987). These profiles are partial projections of a sample of genes. One of the uses of markers in general is to exclude, or alternatively include, potential parents as contributing to offspring.

Phenotypic traits characteristic of the expression of a genetic complement of this invention are distinguishable by electrophoretic separation of DNA sequences cleaved by various restriction endonucleases. Those traits (genetic markers) are termed RFLP (restriction fragment length polymorphisms).

Restriction fragment length polymorphisms (RFLPs) are genetic differences detectable by DNA fragment lengths, typically revealed by agarose gel electrophoresis, after restriction endonuclease digestion of DNA. There are large numbers of restriction endonucleases available, characterized by their nucleotide cleavage sites and their source, e.g., the bacteria E. coli. Variations in RFLP's result from nucleotide base pair differences which alter the cleavage sites of the restriction endonucleases, yielding different sized fragments.

Means for performing RFLP analyses are well known in the art. Restriction fragment length polymorphism analyses reported herein were conducted by Linkage Genetics. This service is available to the public on a contractual basis. Probes were prepared to the fragment sequences, these probes being complementary to the sequences thereby being capable of hybridizing to them under appropriate conditions well known to those skilled in the art. These probes were labelled with radioactive isotopes or fluorescent dyes for ease of detection. After the fragments were separated by size, they were identified by the probes. Hybridization with a unique cloned sequence permits the identification of a specific chromosomal region (locus). Because all alleles at a locus are detectable, RFLPs are codominant alleles, thereby satisfying a criteria for a genetic marker. They differ from some other types of markers, e.g, from isozymes, in that they reflect the primary DNA sequence, they are not products of transcription or translation. Furthermore, different RFLP genetic marker profiles result from different arrays of restriction endonucleases.

The RFLP genetic marker profile of parental inbred FBLL and hybrids DK512, DK522, DK554, DK570, DK591, and DK623 were determined. Because an inbred is essentially homozygous at all relevant loci, an inbred should, in almost all cases, have only one allele at each locus. In contrast, a diploid genetic marker profile of a hybrid should be the sum of those parents, e.g., if one inbred parent had the allele A at a particular locus, and the other inbred parent had B, the hybrid is AB by inference. An RFLP genetic marker profile of FBLL is presented in Table 5 below.

TABLE 5

RFLP PROFILE OF FBLL

| Probe/Enzyme Combination | Allelic Pair |
|---|---|
| M0264H | GG |
| M0285E | DD |
| M0306H | AA |
| M0445E | BB |
| M1120S | DD |
| M1234H | DD |
| M1238H | FF |
| M1401E | AA |
| M1406H | AA |
| M1447H | AA |
| M1B725E | BB |
| M2297H | AA |
| M2298E | BB |
| M2402H | EE |
| M3296H | AA |
| M3432H | HH |
| M3457E | EE |
| M3B815H | BB |
| M4386H | DD |
| M4396E | AA |
| M4444H | AA |
| M4451H | CC |
| M4UMC19H | BB |
| M4UMC31E | CC |
| M5213S | AA |
| M5288E | CC |
| M5295E | DD |
| M5408H | AA |
| M5409H | CC |
| M5UMC95H | AA |
| M6223E | CC |
| M6252H | EE |

TABLE 5-continued

RFLP PROFILE OF FBLL

| Probe/Enzyme Combination | Allelic Pair |
|---|---|
| M6280H | BB |
| M6373E | EE |
| M7263E | CC |
| M7391H | AA |
| M7433E | AA |
| M7455H | BB |
| M8107S | CC |
| M8110S | DD |
| M8114E | BB |
| M8268H | BB |
| M8438E | AA |
| M8UMC48E | AA |
| M9209E | AA |
| M9211E | GG |
| M9B713S | AA |
| M9BZE | BB |
| M9WAXE | BB |

*Probes used to detect RFLPs are from Linkage Genetics, 1515 West 2200 South, Suite C, Salt Lake City, Utah 84108.

Another aspect of this invention is a plant genetic complement characterized by a genetic isozyme typing profile. Isozymes are forms of proteins that are distinguishable, for example, on starch gel electrophoresis, usually by charge and/or molecular weight. The techniques and nomenclature for isozyme analysis are described in, Stuber, C. W., et al., *Techniques and scoring procedures for starch gel electrophoresis of enzymes of maize C. Zea mays. L.*, Tech. Bull. 286, N. Carolina Agric. Res. Serv. (1988) which is incorporated by reference.

A standard set of loci can be used as a reference set. Comparative analysis of these loci is used to compare the purity of hybrid seeds, to assess the increased variability in hybrids compared to inbreds, and to determine the identity of seeds, plants, and plant parts. In this respect, an isozyme reference set can be used to develop genotypic "fingerprints." Table 6 lists the identifying numbers of the alleles at isozyme loci types and is an exemplary genetic isozyme typing profile for FBLL.

TABLE 6

ISOZYME PROFILE FOR FBLL

| LOCUS | ISOZYME ALLELES |
|---|---|
| Acph-1 | 2 |
| Cat-3 | 9 |
| Got-1 | 4 |
| Got-2 | 4 |
| Got-3 | 4 |
| Idh-1 | 4 |
| Idh-2 | 4 |
| Mdh-1 | 6 |
| Mdh-2 | 3.5 |
| Mdh-3 | 16 |
| Mdh-4 | 12 |
| Mdh-5 | 12 |
| 6-Pgd-1 | 3.8 |
| 6-Pgd-2 | 5 |
| Pgm-1 | 9 |
| Pgm-2 | 4 |
| Phi-1 | 4 |
| # Seeds Analyzed | 24 |

The present invention also contemplates a hybrid genetic complement formed by the combination of a haploid genetic complement of the corn plant FBLL with a haploid genetic complement of a second corn plant. Means for combining a haploid genetic complement from FBLL with another haploid genetic complement can be any method hereinbefore for producing a hybrid plant from FBLL. It is also contemplated that a hybrid genetic complement can be prepared using in vitro regeneration of a tissue culture of a hybrid plant of this invention.

A hybrid genetic complement contained in the seed of a hybrid derived from FBLL is a further aspect of this invention. Exemplary hybrid genetic complements are the genetic complements of hybrids DK512, DK522, DK554, DK570, DK591, and DK623. Table 7 shows the identifying numbers of the alleles for hybrids DK512, DK522, DK554, DK570, DK591, and DK623, and is an exemplary RFLP genetic markers profile of hybrids of FBLL.

TABLE 7

RFLP PROFILE FOR DK512, DK522, DK554, DK570, DK591, and DK623

| PROBE/ MARKER | ALLELIC PAIR | | | | | |
|---|---|---|---|---|---|---|
| | DK512 | DK522 | DK554 | DK570 | DK591 | DK623 |
| M0264H | GH | FG | GH | GL | EG | GM |
| M0285E | — | DD | — | DD | — | — |
| M0306H | AA | AC | AA | AA | AA | AF |
| M0445E | AB | BD | — | BC | BD | AB |
| M1120S | DE | DF | BD | BD | BD | BD |
| M1234H | DI | AD | — | — | DE | BD |
| M1238H | EF | FF | EF | FI | EF | EF |
| M1401E | AC | AA | AA | AA | AA | AB |
| M1406H | AB | AA | AB | AA | AB | AA |
| M1447H | AB | AB | AA | AA | AA | AA |
| M1B725E | BB | BH | BB | — | BH | BB |
| M2297H | AB | AD | AC | AD | AC | AC |
| M2298E | BC | BB | BC | AB | BC | AB |
| M2402H | CE | DE | EE | DE | EE | EE |
| M3296H | ACE | AC | AA | AA | AE | AA |
| M3432H | AH | DH | DH | HH | FH | DH |
| M3457E | CE | CE | CE | DE | EE | DE |
| M3B815H | BC | BC | BC | — | BB | BD |
| M4386H | DD | BD | DD | BD | AD | BD |
| M4396E | AH | AB | AFH | AB | AH | AB |
| M4444H | AA | AA | AA | AA | AG | AA |
| M4451H | BC | BC | BC | AC | BC | ABC |
| M4UMC19H | AB | AB | AB | BC | AB | BC |
| M4UMC31E | BC | CC | BC | CC | CC | BC |
| M5213S | AA | AA | AB | AA | AA | AA |
| M5288E | — | BC | — | BC | — | — |
| M5295E | ADI | CD | CD | CD | CD | CD |
| M5408H | AB | AA | AA | AA | AA | AA |
| M5409H | CC | CC | CC | CC | CC | CC |
| M5UMC95H | AB | AB | AC | AC | AD | AC |
| M6223E | CC | CC | CC | CC | BC | CC |
| M6252H | AE | AE | AE | AE | AE | AE |
| M6280H | BC | BF | — | BE | BC | BI |
| M6373E | EE | DE | AE | — | AE | AE |
| M7263E | AC | CC | — | CC | BC | CC |
| M7391H | AA | AA | AC | AA | AC | AA |
| M7433E | — | AC | — | AC | — | — |
| M7455H | BB | BB | BB | BB | AB | BB |
| M8107S | AC | CD | CE | CD | CF | |
| M8110S | AD | AD | AD | AD | ACD | CD |
| M8114E | BB | BD | BB | BD | BE | BD |
| M8268H | BL | BC | AB | BC | BB | BC |
| M8438E | AD | AB | AB | AB | AB | AC |
| M8UMC48E | AA | ABC | AC | AD | AC | AC |
| M9209E | AA | AA | AA | AA | AA | AA |
| M9211E | CG | AG | CG | AG | CG | AG |
| M9B713S | AA | AA | AB | AB | AB | AB |
| M9BZE | AB | BB | AB | BB | AB | BB |
| M9WAXE | BB | AB | AB | AB | BG | AB |

*Probes used to detect RFLPs are from Linkage Genetics, 1515 West 2200 South, Suite C, Salt Lake City, Utah 84119.

A hybrid genetic complement of the present invention can also be exemplified using a genetic isozyme typing profile. Profiles for hybrids DK512, DK522, DK554, DK570, DK591, and DK623 are shown in Table 8.

TABLE 8

ISOZYME PROFILES FOR DK512, DK522, DK554, DK570, DK591, and DK623

| LOCUS | ISOZYME ALLELES | | | | | |
|---|---|---|---|---|---|---|
| | DK512 | DK522 | DK554 | DK570 | DK591 | DK623 |
| Acph-1 | 2 | 2/3 | 2/3 | 2/4 | 2 | 2/4 |
| Adh-1 | 4 | 4 | 4 | 4 | 4 | 4 |
| Amp-1 | — | — | — | 4 | — | — |
| Cat-3 | 9 | 9 | 9 | 9 | 9 | 9 |
| Dia-1 | — | — | 8 | 8/12 | — | — |
| Dia-2 | — | — | 4 | 4 | — | — |
| Gdh-1 | — | — | 1 | — | — | — |
| B-Glu-1 | — | — | — | 7 | — | — |
| Got-1 | 4 | 4 | 4 | 4 | 4 | 4 |
| Got-2 | 4 | 4 | 4 | 4 | 4 | — |
| Got-3 | 4 | 4 | 4 | 4 | 4 | — |
| Hex-2 | — | — | — | 2 | — | — |
| Idh-1 | 4 | 4 | 4 | 4 | 4 | 4 |
| Idh-2 | 4/6 | 4 | 4/6 | 4/6 | 4/6 | 4 |
| Mdh-1 | 6 | 6 | 1/6 | 6 | 6 | 6* |
| Mdh-2 | 3.5 | 3.5/6 | 3.5 | 3.5/6 | 3.5 | 3.5/6 |
| Mdh-3 | 16 | 16 | 16 | 16 | 16 | 16 |
| Mdh-4 | 12 | 12 | 12 | 12 | 12 | 12 |
| Mdh-5 | 12 | 12 | 12 | 12 | 12 | 12 |
| 6-Pgd-1 | 3.8 | 3.8 | 3.8 | 2/3.8 | 3.8 | 2/3.8 |
| 6-Pgd-2 | 5 | 5 | 5 | 5 | 5 | 5 |
| Pgm-1 | 9 | 9 | 9 | 9 | 9 | 9 |
| Pgm-2 | 4 | 4 | 4 | 4 | 4 | 4 |
| Phi-1 | 4 | 4 | 4 | 4 | 4 | 4 |
| Tpi-1 | — | — | 4 | 4 | — | — |
| Tpi-2 | — | — | 4 | 4 | — | — |
| Tpi-3 | — | — | 4 | 4 | — | — |
| Tpi-4 | — | — | 4 | 4 | — | — |
| #Seeds Analyzed | 6 | 6 | 6 | 6 | 6 | 6 |

*Allele is probably 6, but null cannot be ruled out.

The foregoing illustrative embodiments are not limiting of the specification or claims in any way. Changes, modifications, and alterations can be made to those embodiments without departing from the true scope and spirit of the invention.

What is claimed is:

1. A purified population of hybrid seed having corn plant FBLL as one inbred parent, a sample of the seed of said corn plant FBLL, having been deposited under ATCC accession No. PTA-3713.

2. The purified population of hybrid seed of claim 1, wherein the hybrid seed is produced by crossing corn plant FBLL with a second corn plant, a sample of the seed of said corn plant FBLL having been deposited under ATCC accession No. PTA-3713.

3. The purified population of hybrid seed of claim 1, wherein crossing comprises the steps of:

(a) planting in pollinating proximity seed of said corn plant FBLL and said second corn plant;

(b) growing the seeds of the corn plant FBLL and the second corn plant into plants that bear flowers;

(c) emasculating a flower of either the corn plant FBLL or the second corn plant to produce an emasculated parent corn plant;

(d) allowing cross-pollination to occur between the corn plant FBLL and the second corn plant; and (e) harvesting hybrid seeds produced on said emasculated parent corn plant.

4. A population of hybrid corn plants produced by growing the seed of claim 1.

5. A tissue culture of regenerable cells of corn plant FBLL, which plant has ATCC accession No. PTA-3713, wherein the tissue regenerates plants having all the physiological and morphological characteristics of corn plant FBLL.

6. A tissue culture according to claim 5, the tissue culture initiated from the group consisting of embryos, meristematic cells, pollen, leaves, anthers, roots, root tips, silk, flowers, kernels, ears, cobs, husks, stalks and protoplasts thereof.

7. A corn plant regenerated from the tissue culture of claim 5, and having all the physiological and morphological characteristics of corn plant FBLL.

* * * * *

UNITED STATES PATENT AND TRADEMARK OFFICE
CERTIFICATE OF CORRECTION

PATENT NO.     : 6,362,403 B1
DATED          : March 26, 2002
INVENTOR(S)    : John H. Pfund It is certified that error appears in the above-identified patent and that said Letters Patent is hereby corrected as shown below:

<u>Title page,</u>
Item [57], ABSTRACT,
Line 11, please delete "corn," and insert -- corn -- therefor.

Signed and Sealed this

Twenty-seventh Day of August, 2002

*Attest:*

*Attesting Officer*

JAMES E. ROGAN
*Director of the United States Patent and Trademark Office*